(12) United States Patent
Adachi et al.

(10) Patent No.: US 7,472,036 B2
(45) Date of Patent: Dec. 30, 2008

(54) SERVICE PROVIDING SYSTEM, SERVICE PROVIDING METHOD, AND PROGRAM

(75) Inventors: Shinobu Adachi, Osaka (JP); Koji Morikawa, Kyoto (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 11/666,241

(22) PCT Filed: Jun. 21, 2006

(86) PCT No.: PCT/JP2006/312410

§ 371 (c)(1),
(2), (4) Date: Apr. 25, 2007

(87) PCT Pub. No.: WO2007/013241

PCT Pub. Date: Feb. 1, 2007

(65) Prior Publication Data

US 2008/0097719 A1 Apr. 24, 2008

(30) Foreign Application Priority Data

Jul. 26, 2005 (JP) .............................. 2005-215697

(51) Int. Cl.
*G06F 15/00* (2006.01)
(52) U.S. Cl. .................. 702/127; 702/82; 707/104.1
(58) Field of Classification Search .................. 702/82, 702/127, 186–190; 707/3, 7, 104.1; 700/90; 709/203, 227; 713/193; 715/716
See application file for complete search history.

(56) References Cited

U.S. PATENT DOCUMENTS

2006/0101079 A1* 5/2006 Morikawa et al. ........ 707/104.1

FOREIGN PATENT DOCUMENTS

| JP | 8-117199 A | 5/1996 |
| JP | 10-80409 A | 3/1998 |
| WO | WO 2005/001677 A1 | 1/2005 |

OTHER PUBLICATIONS

Shigeto Nishida et al., "Hypothesis Test of Physiological Variability for Peak Latency and Its Interval Estimate in the Evoked Potential," Publication of Electronics, Information and System Society, vol. 118-C No. 2, 1998, pp. 129-136.

(Continued)

*Primary Examiner*—John H Le
(74) *Attorney, Agent, or Firm*—McDermott Will & Emery LLP

(57) ABSTRACT

A judgment section (200) judges the presence or absence of a specific event-related potential in an event-related potential of user's (50) electroencephalogram measured by a biological signal detection section (101). A judgment standard storage section (203) stores a plurality of judgment standards according to the number of occurrences of the specific event-related potential. A user's state judging section (201) obtains the number of occurrences of the specific event-related potential by referring to a judgment result storage section (20) and selects any of the judgment standards in the judgment standard storage section (203) according to the obtained number of occurrences thereof for judgment.

7 Claims, 21 Drawing Sheets

OTHER PUBLICATIONS

Jill Cohen et al., "Short Communication On the number of trials needed for P300," International Journal of Psychophysiology 25, pp. 249-255, 1997.

Kaga et al., "Manual of Event-related Potentials (ERP)—Focusing on P300-," published by Shinohara Shuppan Shinsha, 1995.

"Guideline Proposal of Evoked Potential Measurement," revised in 1997, pp. 1-16.

Kenichiro Ishijima et al., "Life Media: Structuring & summarization of personal experience imaging," The Institute of Electronics, Information and Communication Engineers, Technical Report of IEICB., pp. 85-92, 2001.

* cited by examiner

FIG.2

| Time D/M/Y h/m/s | User's reply | Disappointment or non-disappointment | Number n of repetition times of disappointment |
|---|---|---|---|
| 24/03/05 15:43:25 | C | 1 | 1 |
| 24/03/05 15:43:38 | D | 0 | 0 |
| 24/03/05 15:45:21 | B | 1 | 2 |
| 24/03/05 15:46:06 | B | 1 | 3 |
| 24/03/05 15:52:28 | A | 0 | 0 |
| 24/03/05 15:53:00 | D | 0 | 0 |
| 24/03/05 15:59:12 | B | 1 | 4 |
| 24/03/05 16:11:19 | C | 0 | 0 |
| 24/03/05 16:13:32 | A | 1 | 5 |
| ... | | ... | ... |

\* appears above columns for values: 1, 2, 3, 4, 5

FIG.3

| Time | Non-disappointment template | Disappointment templates | | | |
|---|---|---|---|---|---|
| | | Template1 n≤4 | Template2 n≤8 | Template3 n≤12 | Template4 n>12 |
| 200ms | -3.62 | -1.16 | -4.37 | -2.64 | -4.52 |
| 201ms | -3.59 | -1.00 | -4.15 | -2.44 | -4.57 |
| 202ms | -3.55 | -0.85 | -3.92 | -2.24 | -4.61 |
| 203ms | -3.51 | -0.69 | -3.68 | -2.04 | -4.65 |
| 204ms | -3.47 | -0.53 | -3.43 | -1.83 | -4.69 |
| 205ms | -3.43 | -0.38 | -3.18 | -1.63 | -4.72 |
| 206ms | -3.39 | -0.24 | -2.91 | -1.43 | -4.75 |
| 207ms | -3.35 | -0.10 | -2.64 | -1.24 | -4.78 |
| 208ms | -3.31 | 0.03 | -2.37 | -1.06 | -4.81 |
| 209ms | -3.27 | 0.15 | -2.10 | -0.88 | -4.83 |
| 210ms | -3.24 | 0.26 | -1.83 | -0.71 | -4.85 |
| ... | ... | ... | ... | ... | ... |
| 790ms | -6.29 | 3.93 | 1.75 | -4.92 | 0.21 |
| 791ms | -6.36 | 3.93 | 1.77 | -4.96 | 0.27 |
| 792ms | -6.42 | 3.94 | 1.78 | -5.00 | 0.33 |
| 793ms | -6.49 | 3.95 | 1.80 | -5.04 | 0.39 |
| 794ms | -6.55 | 3.96 | 1.82 | -5.07 | 0.45 |
| 795ms | -6.62 | 3.98 | 1.83 | -5.10 | 0.50 |
| 796ms | -6.68 | 4.00 | 1.84 | -5.12 | 0.56 |
| 797ms | -6.74 | 4.02 | 1.85 | -5.13 | 0.62 |
| 798ms | -6.80 | 4.05 | 1.86 | -5.14 | 0.67 |
| 799ms | -6.86 | 4.07 | 1.86 | -5.14 | 0.73 |
| 800ms | -6.91 | 4.10 | 1.85 | -5.13 | 0.78 |

FIG.4

| Time | Non-disappointment template | Disappointment template |
|---|---|---|
| | | Consecutive disappointment template |
| 200 ms | −3.62 | −3.72 |
| 201 ms | −3.59 | −3.67 |
| 202 ms | −3.55 | −3.61 |
| 203 ms | −3.51 | −3.56 |
| 204 ms | −3.47 | −3.50 |
| 205 ms | −3.43 | −3.45 |
| 206 ms | −3.39 | −3.40 |
| 207 ms | −3.35 | −3.36 |
| 208 ms | −3.31 | −3.32 |
| 209 ms | −3.27 | −3.28 |
| 210 ms | −3.24 | −3.24 |
| ... | ... | ... |
| 790 ms | −6.29 | −3.23 |
| 791 ms | −6.36 | −3.16 |
| 792 ms | −6.42 | −3.08 |
| 793 ms | −6.49 | −3.01 |
| 794 ms | −6.55 | −2.94 |
| 795 ms | −6.62 | −2.88 |
| 796 ms | −6.68 | −2.82 |
| 797 ms | −6.74 | −2.76 |
| 798 ms | −6.80 | −2.71 |
| 799 ms | −6.86 | −2.66 |
| 800 ms | −6.91 | −2.61 |

FIG.5

| Time | Non-disappointment template | Disappointment templates | | | | Consecutive disappointment template |
|---|---|---|---|---|---|---|
| | | Template1 n≤4 | Template2 n≤8 | Template3 n≤12 | Template4 n>12 | |
| 200ms | -3.62 | -1.16 | -4.37 | -2.64 | -4.52 | -3.72 |
| 201ms | -3.59 | -1.00 | -4.15 | -2.44 | -4.57 | -3.67 |
| 202ms | -3.55 | -0.85 | -3.92 | -2.24 | -4.61 | -3.61 |
| 203ms | -3.51 | -0.69 | -3.68 | -2.04 | -4.65 | -3.56 |
| 204ms | -3.47 | -0.53 | -3.43 | -1.83 | -4.69 | -3.5 |
| 205ms | -3.43 | -0.38 | -3.18 | -1.63 | -4.72 | -3.45 |
| 206ms | -3.39 | -0.24 | -2.91 | -1.43 | -4.75 | -3.4 |
| 207ms | -3.35 | -0.10 | -2.64 | -1.24 | -4.78 | -3.36 |
| 208ms | -3.31 | 0.03 | -2.37 | -1.06 | -4.81 | -3.32 |
| 209ms | -3.27 | 0.15 | -2.10 | -0.88 | -4.83 | -3.28 |
| 210ms | -3.24 | 0.26 | -1.83 | -0.71 | -4.85 | -3.24 |
| ... | ... | ... | ... | ... | ... | ... |
| 790ms | -6.29 | 3.93 | 1.75 | -4.92 | 0.21 | -3.23 |
| 791ms | -6.36 | 3.93 | 1.77 | -4.96 | 0.27 | -3.16 |
| 792ms | -6.42 | 3.94 | 1.78 | -5.00 | 0.33 | -3.08 |
| 793ms | -6.49 | 3.95 | 1.80 | -5.04 | 0.39 | -3.01 |
| 794ms | -6.55 | 3.96 | 1.82 | -5.07 | 0.45 | -2.94 |
| 795ms | -6.62 | 3.98 | 1.83 | -5.10 | 0.50 | -2.88 |
| 796ms | -6.68 | 4.00 | 1.84 | -5.12 | 0.56 | -2.82 |
| 797ms | -6.74 | 4.02 | 1.85 | -5.13 | 0.62 | -2.76 |
| 798ms | -6.80 | 4.05 | 1.86 | -5.14 | 0.67 | -2.71 |
| 799ms | -6.86 | 4.07 | 1.86 | -5.14 | 0.73 | -2.66 |
| 800ms | -6.91 | 4.10 | 1.85 | -5.13 | 0.78 | -2.61 |

FIG.7

| | Question | | | | | | | | Correct answer | Importance |
|---|---|---|---|---|---|---|---|---|---|---|
| 1 | What country has Eiffel Tower? | A | Paris | B | Rome | C | London | D | Vienna | A | 5 |
| 2 | What is the largest peninsula in Japan? | A | Shimokita | B | Siretoko | C | Ise | D | Boso | C | 4 |
| 3 | What country has Royal Greenwich Observatory? | A | German | B | England | C | France | D | America | B | 2 |
| 4 | What does "credit" mean? | A | Cash | B | Bank | C | Account | D | Shopping | C | 3 |
| 5 | Which country does not belong to Africa? | A | Nigeria | B | Kenya | C | Guinea | D | Argentine | D | 1 |
| 6 | How many men are there out of 1000 people when women occupy 40%? | A | 400 | B | 500 | C | 600 | D | 700 | C | 4 |
| 7 | Who said "I think; therefore I am"? | A | Plato | B | Socrates | C | Kant | D | Descartes | D | 3 |
| ... | ... | | | | | | | | ... | ... |

FIG.8

| Question No. | User's appreciation degree | | |
|---|---|---|---|
| | First | Second | Third |
| 1 | Appreciation | Appreciation | - |
| 2 | Appreciation | - | - |
| 3 | Guesswork | Guesswork | Appreciation |
| 4 | Delusion | Appreciation | - |
| 5 | Appreciation | Appreciation | - |
| 6 | Non-appreciation | Guesswork | Appreciation |
| 7 | Guesswork | Appreciation | |
| ... | ... | ... | ... |

FIG.9

| | | Disappointment singal | |
|---|---|---|---|
| | | Detected | Not detected |
| User's reply | Correct | Guesswork | Appreciation |
| | Wrong | Delusion | Non-appreciation |

FIG.11

|  |  | Disappointment singal | |
|---|---|---|---|
|  |  | Detected | Not detected |
| User's reply | Correct | 3 | 0.1 |
|  | Wrong | 3 | 3 |

Processing b

SERVICE PROVIDING SYSTEM, SERVICE PROVIDING METHOD, AND PROGRAM

RELATED APPLICATIONS

This application is the U.S. National Phase under 35 U.S.C. § 371 of International Application No. PCT/JP2006/312410, filed on Jun. 21, 2006, which in turn claims the benefit of Japanese Application No. 2005-215697, filed on Jul. 26, 2005, the disclosures of which Applications are incorporated by reference herein.

TECHNICAL FIELD

The present invention relates to a service providing system, a service providing method, and a program which provide appropriate services by measuring an event-related potential of an electroencephalogram and judging whether or not a specific event-related potential is present therein.

BACKGROUND ART

In the case where user's state is estimated in each event (trial) on the basis of an event-related potential and is applied to an appliance, accuracy of user's state estimation based on the event-related potential is significant. As described in Non-patent Document 1, the amplitude of the event-related potential is so small, approximately one tenth of a background electroencephalogram, that it is difficult to identify it by a method of simply subjecting the potential waveform to a threshold processing.

There is listed Patent Document 1 as a conventional technique for applying user's state estimated on the basis of the event-related potential to an interface with an appliance. In Patent Document 1, user's state when user's expectation of appliance's operation is different from actual appliance's operation is defined as disappointment, and user's disappointed state is detected by referring to a disappointment signal component appearing in the event-related potential as an index. Immediate (within approximately 600 ms) detection of the user's disappointment by making use of the feature of the event-related potential achieves interactive service change. In Patent Document 1, disappointment is detected by a discriminant analysis in which a Mahalanobis distance is calculated from a correlation coefficient calculated with the use of an average waveform under a disappointment state obtained by about 20 disappointment samples as a template.

Besides, Patent Document 2 and Patent Document 3 propose techniques for reducing noise mixed with an electroencephalogram signal. In Patent Document 2, a threshold value is determined by frequency analysis, wavelet, template, covariance, or the like. Patent Document 3 refers to a method using a band-pass filter in which reduction in mixed noise is achieved to allow a desired component to be extracted from the electroencephalogram signal.

Patent Document 1: WO2005/001677
Patent Document 2: Japanese Patent Application Laid Open Publication No. 10-80409A
Patent Document 3: Japanese Patent Application Laid Open Publication No. 8-117199A
Non-patent Document 1: Kaga et al., "Manual of Event-related potential (ERP) -Focusing on P300-," published by Shinohara Shuppan Shinsha, 1995
Non-patent Document 2: "Guideline Proposal of Evoked Potential Measurement," revised in 1997

SUMMARY OF THE INVENTION

Problems that the Invention is to Solve

The disappointment signal in Patent Document 1 is an endogenous component reflecting disappointment as difference between user's expectation and an actual result. For this reason, when a trial is performed plural times, a component of the measured disappointment signal may vary from trial to trial according to user's expectation. The present inventors performed actually a below-mentioned experiment for obtaining disappointment signals to find newly that the amplitude and the latency of the disappointment signal component appearing in the event-related potential vary remarkably by several-time repetition of disappointment.

Referring to application of the disappointment signal component to an appliance, disappointment would occur plural times, for example, in the case where a user who does not know how to use an appliance manipulates the appliance, in the case where many questions of which field a user is not good at are presented in learning through a learning system that feedbacks true/false evaluation upon input of a reply, and the like. Under the situation where disappointment occurs plural times, the disappointment signal component varies as described above, so that accuracy of disappointment judgment may lower in the disappointment judgment using a single template as in Patent Document 1. Further, under the situation where the component of the measured signal component varies, it is difficult to extract a desired signal component at high accuracy by the noise reducing method as in Patent Document 2 or Patent Document 3.

In view of the aforementioned problems, the present invention has its object of enabling disappointment judgment at high accuracy even under the situation where a disappointment signal component appearing in an event-related potential varies in plural-time event-related potential measurement.

Means for Solving the Problems

In order to solve the above problems, a service providing system of the present invention includes: an input section which receives a request of a user; an appliance operation control section which determines a response content in response to the request received at the input section; a presentation section which presents to the user the response content determined by the appliance operation control section; a biological signal detection section which measures an event-related potential of an electroencephalogram as a biological signal of the user; and a judgment section which judges presence or absence of a specific related-event potential after a predetermined period beginning at a starting point in the event-related potential measured by the biological signal detection section, the starting point being time when the presentation section presents the response content, wherein the judgment section includes: a judgment result storage section which stores a history of a judgment result; a judgment standard storage section which stores a plurality of judgment standards for judging presence or absence of the specific event-related potential according to number of occurrences of the specific event-related potential; and a user's state judgment section which obtains number of occurrences of the specific event-related potential by referring to the judgment result storage section, which selects one of the judgment standards in the judgment standard storage section according to the obtained number of occurrences, and which judges presence or absence of the specific event-related potential with use of the selected judgment standard.

In the present invention, a plurality of judgment standards according to the number of occurrences of the specific event-related potential are stored in the judgment standard storage section so that the presence or absence of the specific event-related potential is judged with the use of a judgment standard according to the number of occurrences of the specific event-related potential. Accordingly, accuracy of user's state estimation increases in the case where a series of processes from user's request to judgment of the presence or absence of the specific event-related potential is performed plural times.

In a preferable embodiment, the judgment standard storage section further stores at least one for-consecutiveness judgment standard for a case where the specific event-related potential occurs consecutively, and the user's state judgment section refers to the judgment result storage section, and when it has been judged that the specific event-related potential is present in the previous judgment, the user's state judgment section selects one of the for-consecutiveness judgment standard in the judgment standard storage section and judges presence or absence of the specific event-related potential with use of the selected for-consecutiveness judgment standard.

The predetermined period is preferably between 450 ms and 800 ms, both inclusive.

The predetermined period is preferably around 600 ms or around 750 ms.

Preferably, the judgment standards are templates prepared on the basis of a result of event-related potential measured in advance.

In a preferable embodiment, the appliance operation control section determines again or cancel the response content according to presence or absence of the specific event-related potential.

A service providing method of the present invention includes: a step A of receiving a request of a user; a step B of determining a response content in response to the request; a step C of presenting the determined response content to the user; a step D of measuring an event-related potential of an electroencephalogram as a biological signal of the user; a step E of judging presence or absence of a specific event-related potential after a predetermined period beginning at a starting point in the measured event-related potential, the starting point being time when the response content is presented, wherein the step E includes: a sub-step of obtaining number of occurrences of the specific event-related potential by referring to a history of a judgment result; and a sub-step of determining, according to the obtained number of occurrences, a judgment standard for judging presence or absence of the specific event-related potential and judging presence or absence of the specific event-related potential with use of the determined judgment standard.

A program of the present invention allows a computer to execute: a step A of receiving a request of a user; a step B of determining a response content in response to the request; a step C of presenting the determined response content to the user; and a step E of judging presence or absence of a specific event-related potential after a predetermined period beginning at a starting point in an event-related potential of a measured electroencephalogram of the user, the starting point being time when the response content is presented, wherein the step E includes: a sub-step of obtaining number of occurrences of the specific event-related potential by referring to a history of a judgment result; and a sub-step of determining, according to the obtained number of occurrences, a judgment standard for judging presence or absence of the specific event-related potential and judging presence or absence of the specific event-related potential with use of the determined judgment standard.

Effects of the Invention

In the present invention, the judgment standard is determined according to the number of occurrences of the specific event-related potential obtained by referring to a history of judgment results. This enables judgment in conformity with the number of occurrences of the specific event-related potential in plural-time trial, increasing accuracy of the identification rate and of judgment of user's state.

BRIEF DESCRIPTION OF THE DRAWINGS

FIG. 2 is a table indicating a concrete example of a history stored in a judgment result database 202.

FIG. 3 indicates one concrete example of templates stored in a user's state judgment section 201.

FIG. 4 indicates another concrete example of templates stored in the user's state judgment section 201.

FIG. 5 indicates still another concrete example of templates stored in the user's state judgment section 201.

FIG. 7 is a table indicating a concrete example of information stored in a question database 303, such as questions.

FIG. 8 is a table indicating concrete examples of user's appreciation states accumulated in a result accumulation database 304.

FIG. 9 is a table indicating a judgment logic in a guesswork/delusion judgment section in FIG. 1.

FIG. 11 is a table indicating examples of weighting coefficients accumulated as reply results.

Figure 1:
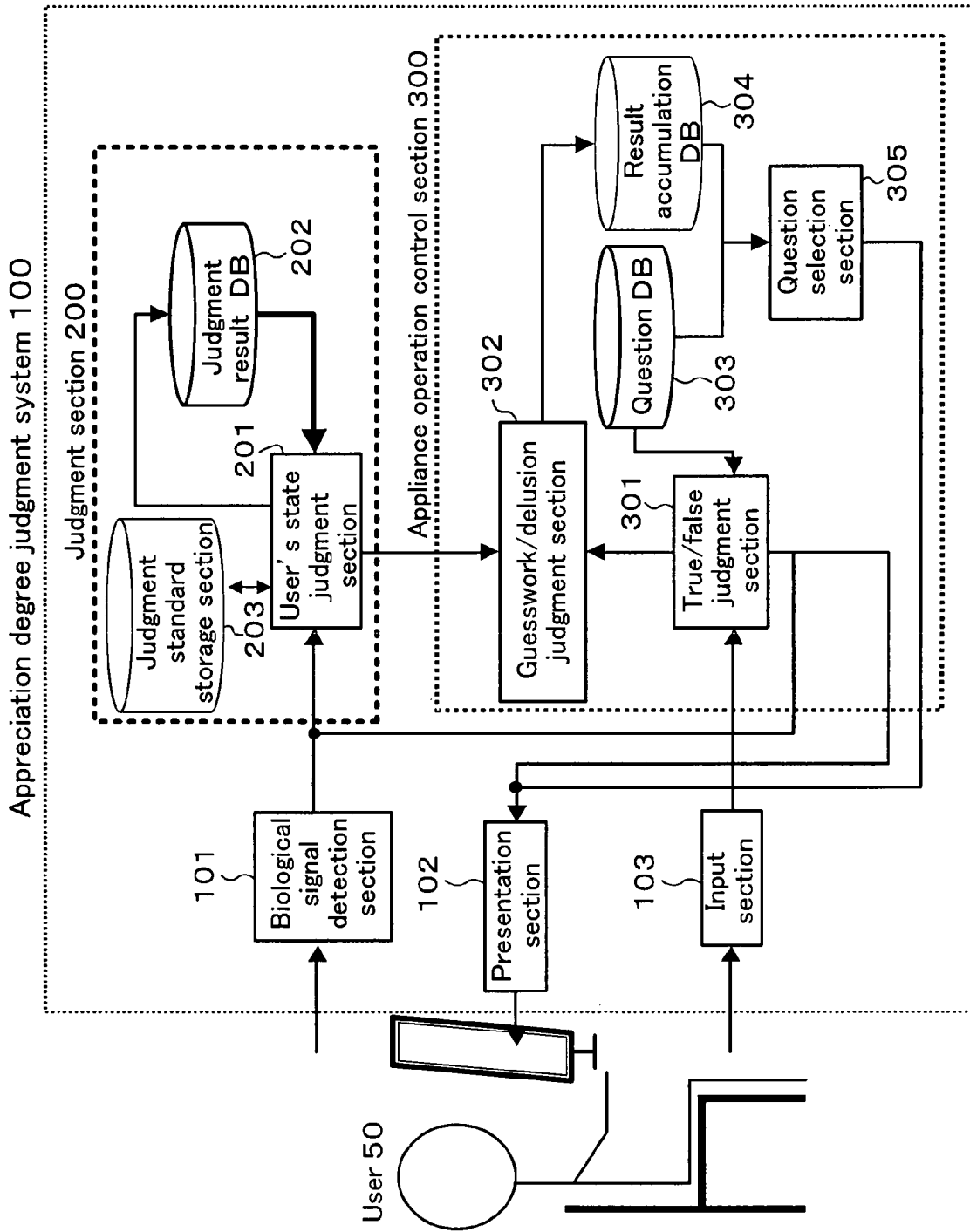
FIG. 1 is an illustration showing a construction of an appreciation degree judgment system according to Embodiment 2.

EXPLANATION OF REFERENCE NUMERALS 1 service providing system
10 input section
11 output section (presentation section)
20 judgment result storage section
100 appreciation degree judgment system (service providing system)
  101 biological signal detection section
  102 presentation section
  103 input section
  200 judgment section
  201 user's state judgment section
  202 judgment result database (judgment result storage section)
  300 appliance operation control section
  301 true/false judgment section
  302 guesswork/delusion judgment section
  303 question database
  304 result accumulation database
  305 question selection section
500 service providing system
  501 response content determination section

BEST MODE FOR CARRYING OUT THE INVENTION

Embodiments of the present invention will be described below with reference to the accompanying drawings. In the drawings referred to below, the same reference numerals are assigned to constitutional elements having substantially the same functions for the sake of simple explanation.

The process of reaching the present invention will be described first. The present inventors performed an experiment for obtaining below-mentioned disappointment signals (specific event-related potentials), which will be described later, to find newly that the amplitude and the latency of the disappointment signal component appearing in the event-related potential vary by several-time repetition of disappointment. Disappointment would occur plural times, for example, when a user who does not know how to use an appliance manipulates the appliance, when many questions of which field a user is not good at are presented in learning through a learning system that feedbacks true/false evaluation upon input of a reply, or the like. Under such a situation, disappointment judgment using a single judgment standard as in Patent Document 1 may lower the identification rate. Under the circumstances, the present inventors contemplated highly accurate disappointment judgment by changing the judgment standard according to transition of user's state in the case where disappointment would occur plural times.

Next, the experiment for obtaining disappointment signals that the present inventors performed will be described, and then, the facts will be shown that repetition of disappointment makes the disappointment signal to vary actually and that change in judgment standard according to transition of user's state increases the identification rate.

(Experiment for Obtaining Disappointment Signals)

Figure 14:
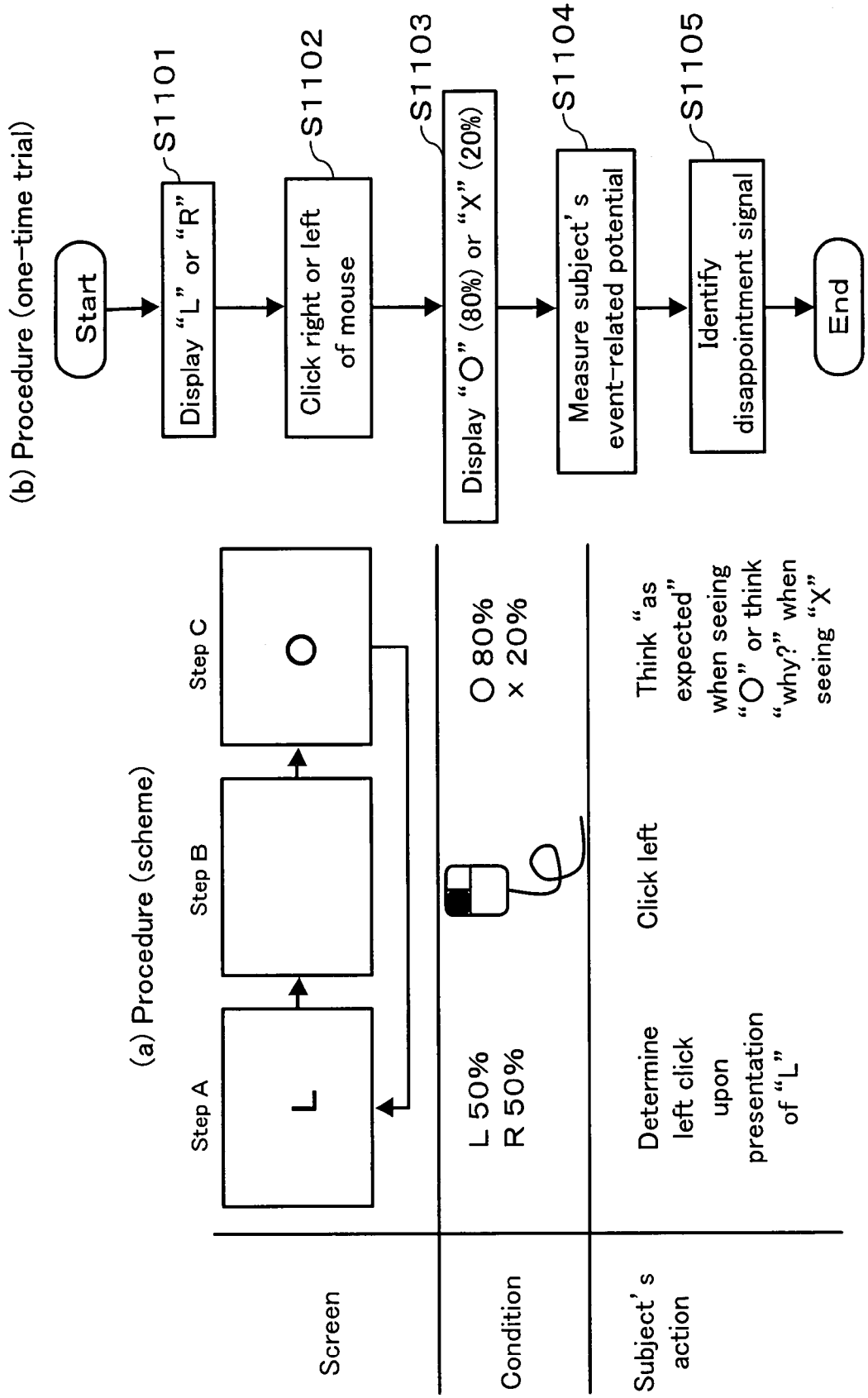
FIG. 14(a) is a schematic illustration showing a procedure for an experiment that the present inventors performed.
FIG. 14(b) is a flowchart depicting a procedure for one-time trial of the experiment.

FIG. 14(a) is an illustration schematically showing a procedure for the experiment. In this experiment, the procedure includes: a step A of providing an instruction to a subject; a step B of allowing the subject imagining necessary action upon receipt of the instruction to manipulate an appliance; and a step C of presenting to the subject an operation as a result of the manipulation.

First, the experimenter explains a subject that a letter "L" or "R" will be displayed on a screen and told him/her to click left of a mouse when the letter "L" is displayed and to click right thereof when the letter "R" is displayed. Then, the letter "L" or "R" is selected at random at a possibility of 50% and is displayed on the screen (the step A). The subject looks at the displayed letter and clicks left or right of the mouse in compliance with the told rule (the step B). Then, whether or not the subject has clicked correctly is indicated through a sign "◯" or "X" to the subject (the step C). Namely, the mouse serves as an input section that receives user's request (left click or right click), and the screen serves as a presentation section for presenting a response content ("◯" or "X").

Wherein, in the experiment, even though the subject clicks correctly (the subject might click almost 100% correctly), "X" is displayed at a possibility of 20%. This resulted in about 20-time repetition of a disappointment trial in which "X" is displayed in response to a correct reply. In the experiment, a plurality of subjects were subjected to 30-time trial in which "◯" is always displayed as a practice, and then, were subjected to 100-time trial according to the procedure depicted in FIG. 14(b).

FIG. 14(b) is a flowchart depicting the procedure for one-time trial. First, the letter "L" or "R" is selected at a possibility of 50% and is displayed (S1101), and then, a subject looks at the letter, determines which button should be clicked, and manipulates the mouse (S1102). In response to the subject's manipulation, "◯" or "X" is displayed on the basis of whether or not the manipulation has been correct. Wherein, "X" is displayed at a possibility of 20% even when "◯" should be displayed (S1103). The event-related potential in subject's electroencephalogram is measured from a timing as a starting point when "◯" or "X" is displayed (S1104), and the measured event-related potential is processed to identify the disappointment signal (S1105).

Figure 15:
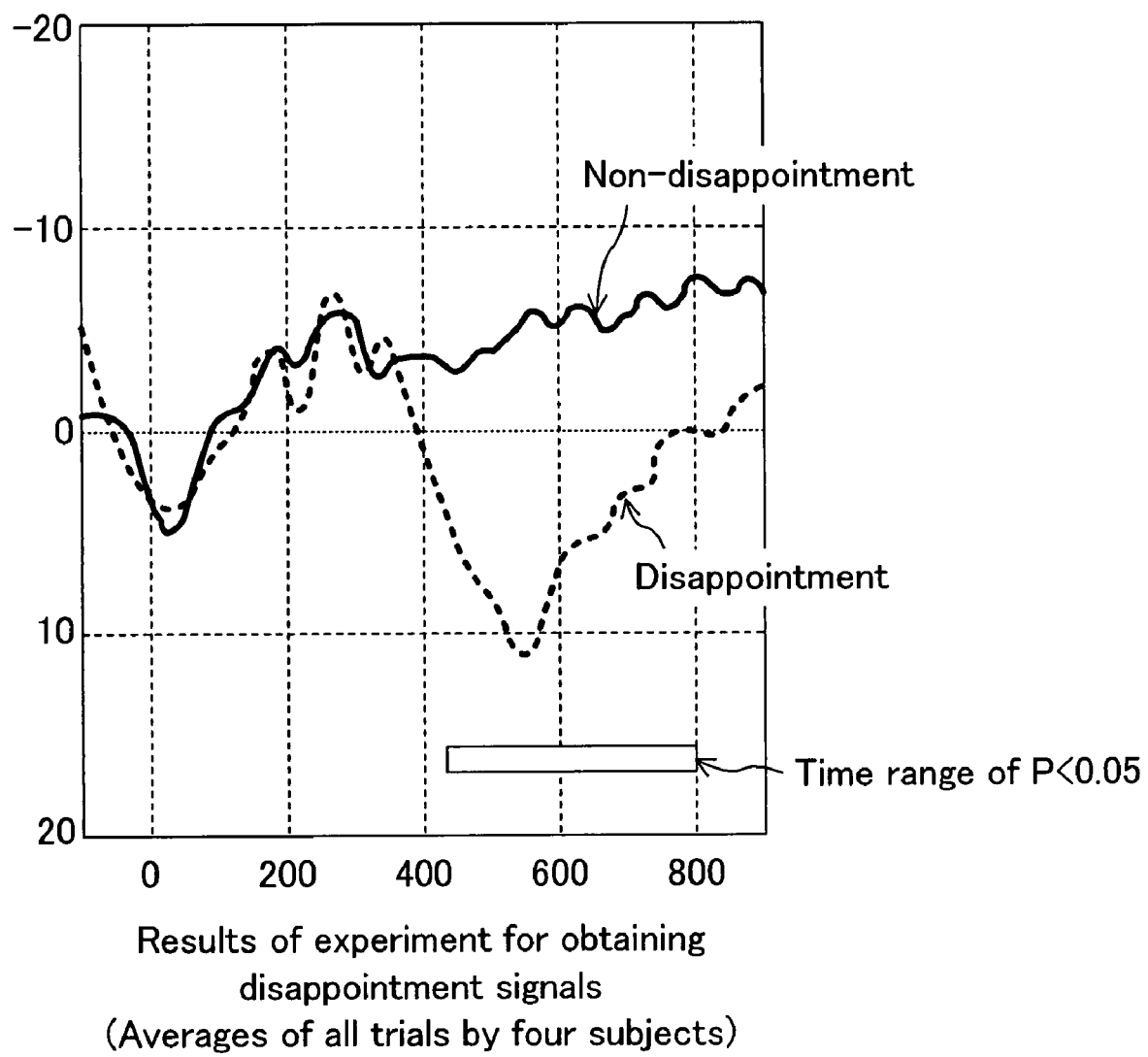
FIG. 15 is a graph showing waveforms obtained by totally averaging event-related potential data in the experiment on four subjects.

FIG. 15 is a graph showing waveforms as the experimental result obtained by totally averaging experimental data of four subjects. The graph of FIG. 15 is obtained by averaging 82 potential waveforms in total of the four subjects each subjected to about 20-time trial, which were measured by an electro-encephalograph from a timing as a starting point when "◯" or "X" is presented, wherein the axis of abscissas indicates time after stimulus provision (at display of "◯" or "X") in the unit of ms, and the axis of ordinates indicates potential in the unit of μV. The broken line indicates a waveform with "disappointment," that is, a waveform (disappointment) obtained when "X" is displayed in response to correct click, and the solid line indicates a waveform in usual time, that is, a waveform (non-disappointment) obtained when "◯" is displayed in response to correct click. It is understood from FIG. 15 that upon "disappointment," an event-related potential presenting a characteristic which the waveform in usual time does not present appears at around 600 ms after stimulus provision. Accordingly, it could be inferred that measurement of this event-related potential (specific event-related potential) leads to detection of user's "disappointment state." As a result of t-test performed, significant difference in latency is observed at around 450 to 800 nm ($p<0.05$) between disappointment and non-disappointment. The time range in which the significant difference is observed is indicated in FIG. 15. Wherein, the electrodes are attached in compliance with International 10-20 system at four points of: 1) Pz (the median vertex); 2) and 3) A1 and A2 (auriculars); and 4) body earth (Z) (nasion). The sampling frequency and the band-pass filter are set to 1000 Hz and 0.03 to 100 Hz, respectively.

As cleared from this experiment, distinctive difference is present in the event-related potential measured by the electroencephalograph between when "◯" or "X" is displayed along the subjects, expectation and when it is displayed against the subject's expectation. Accordingly, this event-related potential can be used as a "disappointment signal" for judging user's state.

(Variation in Disappointment Signal)

In the above described experiment for obtaining disappointment signals, disappointment caused by displaying "X" in response to correct reply is repeated about 20 times. For this reason, the subjects would notice in the course of the experiment that disappointment may occur, and would change his/her expectation from expectation that "○" is always displayed in response to correct reply to expectation that "X" may be displayed in spite of correct reply.

Figure 16:
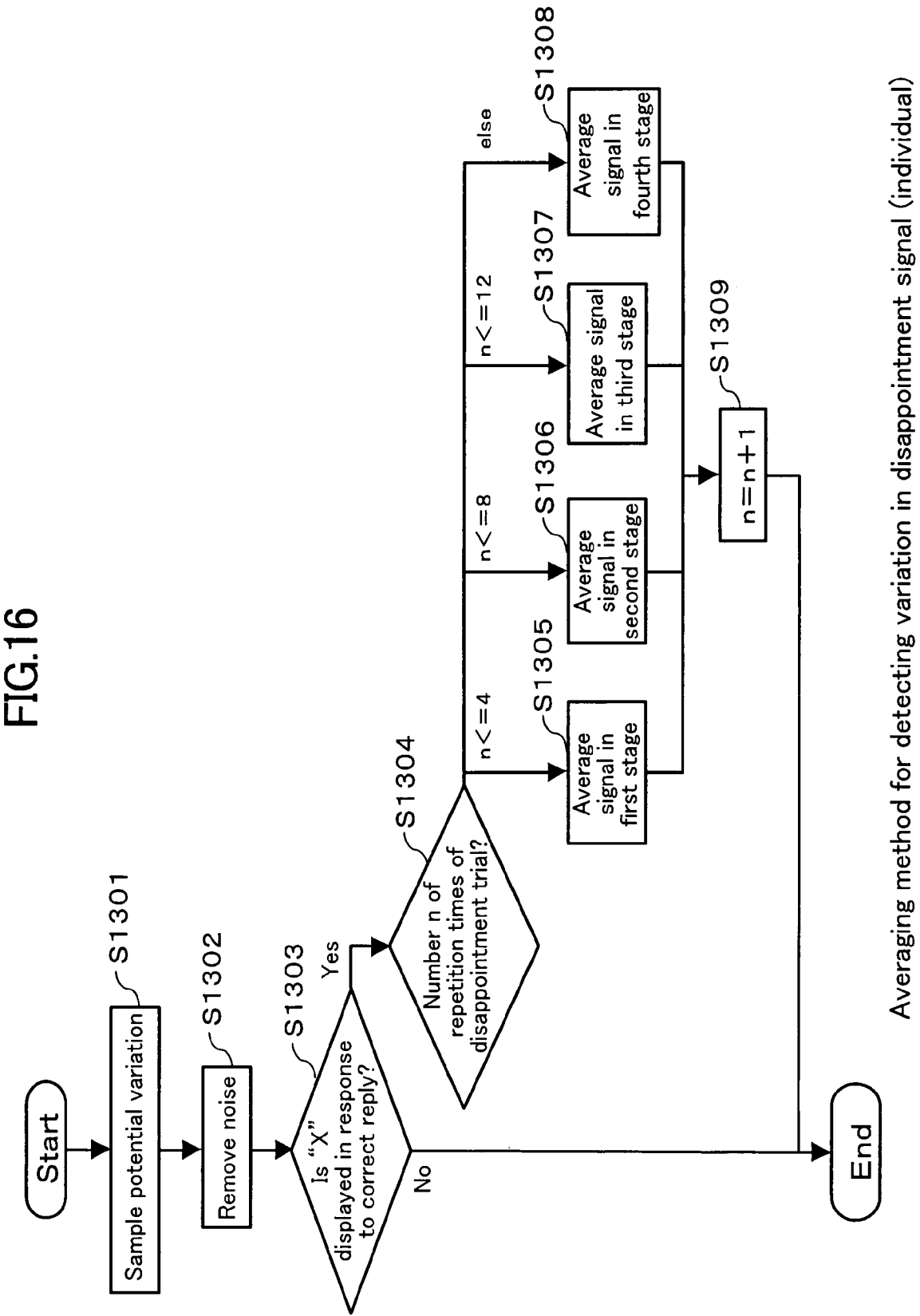
FIG. 16 is a flowchart depicting a procedure for preparing to-be-changed templates as judgment standards.

With the above fact taken into consideration, a processing as depicted in the flowchart of FIG. 16 was performed for examining variation in disappointment signal in association with repetition of disappointment.

A step S1301 is a step of sampling potential variation in an electroencephalogram from a timing as a starting point when a response content ("○" or "X") is output (at response presentation). The sampling frequency may be 200 Hz, 500 Hz, 1000 Hz, or the like, for example.

A step S1302 is a step of removing noise from the potential varying waveform sampled in the step S1301. Herein, the potential varying waveform is allowed to pass through a band-pass filter of, for example, 0.03 to 30 Hz for cutting low frequency components and high frequency components which are mixed with the signal, or a waveform having an amplitude of 80 μV or larger is removed from the to-be-identified target for reducing influence by blinking and eye movement.

A step S1303 is a step of judging whether or not "X" is presented in response to a correct reply (right or left click) in the above-described experiment for obtaining disappointment signals, namely, whether or not it is a disappointment trial (judging the presence or absence of the specific event-related potential). When "X" is presented in response to a correct reply, the routine proceeds to a step S1304. Otherwise, namely, when "○" is presented thereto, the routine proceeds to End.

A step S1304 is a step of determining, according to the number n of repetitions of the disappointment trial, in which stage the disappointment signal in this time should be averaged in order to examine how the disappointment signal varies in association with repletion of disappointment. Steps S1305 to S1308 are steps of averaging the disappointment signal in first (initial), second, third, and fourth (final) stages, respectively. It is noted that, in the step S1304, the number n of repetitions of the disappointment trial for each subject ranges from one to four in the first stage, from five to eight in the second stage, from nine to 12 in the third stage, and 13 or larger in the fourth stage. A step S1309 is a step of incrementing the number of times of the disappointment trial.

Execution of the steps from S1301 through to S1309 with the use of data obtained from the four subjects attains averages of 16-time disappointment trial in each stage where disappointment is repeated substantially the same times. Herein, for examining time variation in waveform from data in which the number of averaging times is sufficient in each stage, the number of repetitions of the disappointment trial is divided into four stages by each four-time trial with the number of subjects, the number of repetitions of the performed trial taken into consideration.

Figure 17:
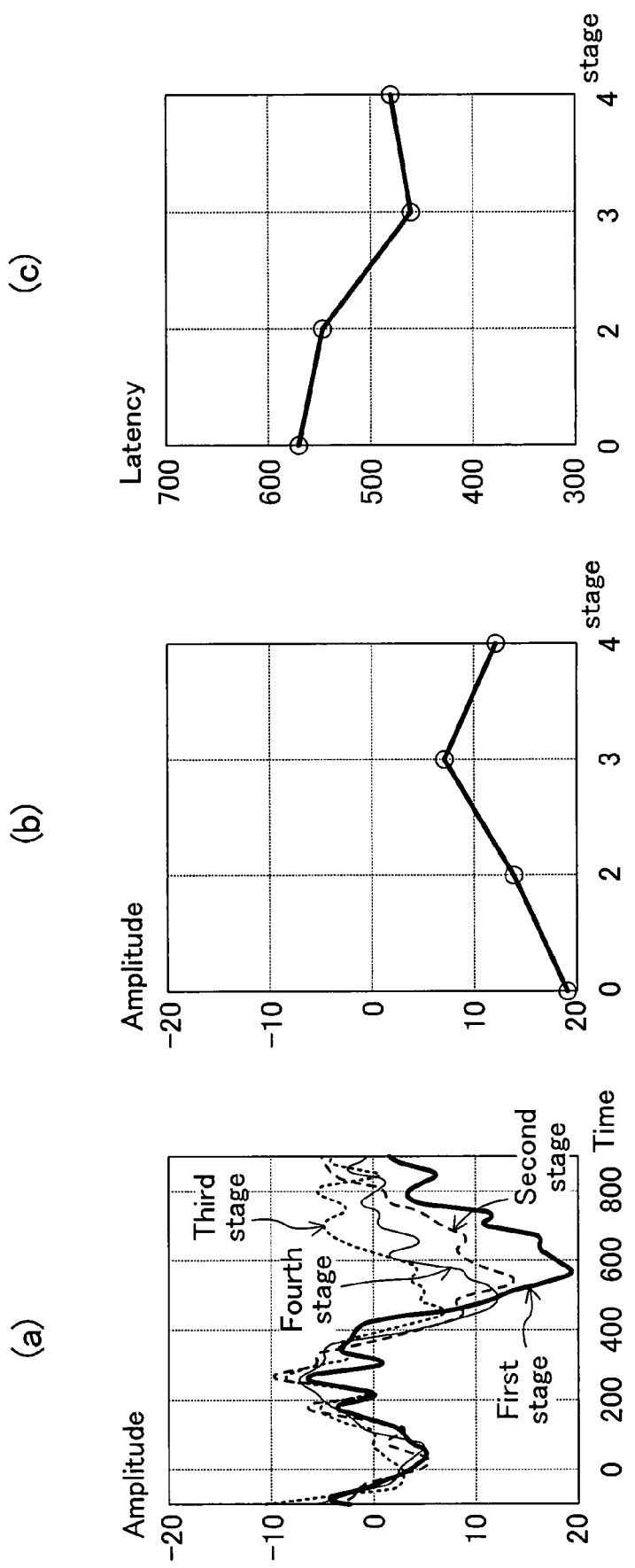
FIG. 17 is a graph showing variation in disappointment signal components according to the number of occurrences of disappointment.

FIG. 17 shows time variation of disappointment signal component obtained by averaging the disappointment signals in each stage. FIG. 17(a) shows average waveforms of the disappointment signals in the respective stages, wherein the axis of abscissas indicates time in the unit of ms while the axis of ordinates indicates potential in the unit of μV. Though the amplitudes and latencies of the disappointment signals in the respective stages differ form one another, tendencies of waveform variation are similar to one another among the respective stages. With only 16-time average at the most in each stage though, the graph can lead to a conclusion that influence of noise component is reduced. FIG. 17(b) is a graph that plots time variation in amplitude (maximum amplitude as the specific event-related potential appearing at around 600 ms) of the disappointment signals in the respective stages, wherein the axis of ordinates indicates potential in the unit of μV. It is understood from the graph that the disappointment signals in the first stage have large amplitudes and that the amplitude decreases as the number of repetitions of disappointment is increased. FIG. 17(c) is a graph that plots latency variation of the disappointment signals in the respective stages, wherein the axis of ordinates indicates time in the unit of ms. It is understood from the graph that the latency is reduced as the number of repetitions of disappointment is increased when compared with those of the disappointment signals in the first stage. As described above, it is revealed that the amplitude and the latency of the specific event-related potential vary largely even in an event in which disappointment signal appears about 20 times in plural-time trial.

As can be read from Page 12, lines 20 to 23 of Non-patent Document 2, in a general oddball task where difference in interval or in image presented is judged, no variation in component of the event-related potential is observed in a trial repeated up to about 20 times. Further, it is reported that less variation in amplitude is observed in a trial repeated up to about 40 times in an oddball task using visual stimulus (J. Cohen, J. Polich, International Journal of Psychophysiology 25, 1997, pp. 249-255 (FIG. 2)). Accordingly, the above variation is a distinctive phenomenon like the disappointment signal component appearing in high-order endogenous brain activity.

(Detection of Disappointment Signal)

The disappointment signal component varies radically even in about 20-time repetition of a disappointment trial at the most. For example, in the case where a user who does not know how to use an appliance manipulates the appliance, the case where many questions of which field a user is not good at are presented in learning through a learning system that feedbacks true/false evaluation upon input of a reply, or the like, disappointment would occur plural times. In such a situation, disappointment judgment using a single template (waveform chart as a judgment standard) as in Patent Document 1 may lower accuracy of disappointment judgment. Under the circumstances, the judgment standard is changed according to the number of repetitions of disappointment to increase the identification rate of disappointment. This method will be described below.

Figure 18:
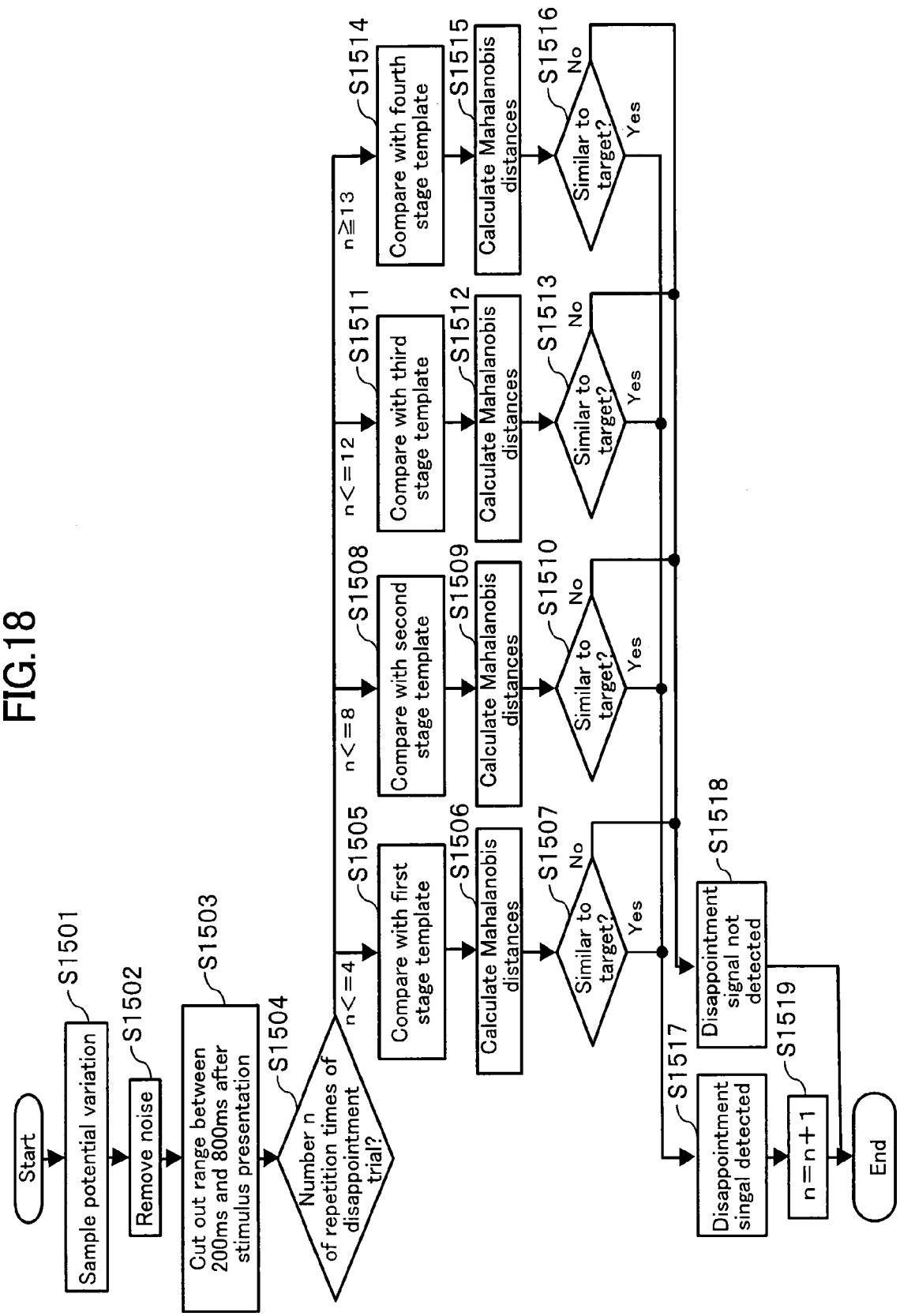
FIG. 18 is a flowchart depicting signal processing of the present invention in which a judgment standard is changed for disappointment signal detection.

FIG. 18 is a flowchart of an example (processing a) of a concrete method for detecting a disappointment signal by changing the judgment standard. There are prepared in advance four standard waveforms (disappointment templates 1 to 4) and a standard template (referred to as a non-disappointment template). The disappointment templates are obtained in the method depicted in FIG. 16, namely, by dividing, according to the number of repetitions of the disappointment trial, disappointment signals of the four subjects into four stages of, for example, the first stage, the second stage, the third stage, and the fourth stage and averaging them in the respective stages. The non-disappointment template is obtained by averaging usual non-disappointment signals. A template is selected from the disappointment templates 1 to 4 according to the number of repetitions of disappointment for use.

Each step of the processing a will be described in order below.

First, variation in event-related potential in the electroencephalogram is sampled from a timing as a starting point when a response content is output (response presentation) (S1501). As the sampling frequency, 200 Hz, 500 Hz, 1000 Hz or the like is used for example.

Next, noise is removed from the sampled potential varying waveform (S1502). Herein, the waveform is allowed to pass through a band-pass filter of, for example, 0.03 to 30 Hz for cutting low frequency components and high frequency components which are mixed with the signal, or a waveform having an amplitude of 80 μV or larger is removed from the to-be-identified target for reducing influence by blinking and eye movement.

Subsequently, a waveform in a region relating to detection of a "disappointment signal" is cut out from the potential varying waveform of the electroencephalogram from which noise is removed (S1503). It has been understood from the above described experimental result that the "disappointment signal" is detected at around 600 ms after stimulus presentation. Further, the waveform in a comparatively earlier range after response presentation appears in response to aural stimulus or visual stimulus and might have no relation to the presence or absence of disappointment. For this reason, it is preferable to remove such a range. Accordingly, the range between, for example, 200 ms and 800 ms after response presentation is cut out.

The range to be cut out is, of course, not limited to the above range and may be set between 450 ms and 800 ms, of which significant difference is admitted by the t-test in the above described experimental result, between 500 ms and 700 ms, between 300 ms and 900 ms, or the like. Alternatively, a range approximately 1 s from response presentation may be cut out with no lower limit set.

Thereafter, a to-be-compared template is determined according to the number of repetitions of the disappointment trial (S1504). Specifically, as will be described later, the number of times that the disappointment signal (the specific event-related potential) is measured is counted in the trial performed until then, and which template should be used is determined according to the number of counted times. For example, when the number n of repetitions of the disappointment trial is one, the disappointment template for the first stage and the non-disappointment template are selected, and then, the measured waveform is compared with the selected templates, and respective correlation coefficients thereof are calculated (S1505). This correlation coefficient calculation calculates to what degree the signal waveform correlates to the respective templates. This step of changing the judgment standard according to the number of repetitions of disappointment is the difference from Patent Document 1.

Subsequently, the distances between the signal waveform and the selected disappointment template for the first stage and between the signal waveform and the non-disappointment template are calculated (S1506). For distance calculation, Mahalanobis distance is employed, for example. Mahalanobis distance indicates a distance to the center of gravity of a group, data of which variance and covariance are taken into consideration (Expression 1). In Expression 1, $D_1^2$ is a square of a Mahalanobis distance to a non-disappointment group, $x_1$ is a correlation coefficient to the non-disappointment template, $x_2$ is a correlation coefficient to a disappointment template, $x_1^{(1)}$ is an average value of the correlation coefficients of the non-disappointment group to the non-disappointment group, $x_2^{(1)}$ is an average value of the correlation coefficients of the non-disappointment group to a disappointment group, and s is a variance/covariance matrix of the non-disappointment group. $D_2^2$, which is a square of a Mahalanobis distance to a disappointment group, is obtained, as well.

[Expression 1]

$$D_1^2(x_1, x_2) = (x_1 - x_1^{(1)}, x_2 - x_2^{(1)}) \begin{bmatrix} s_{11}^{(1)} & s_{12}^{(1)} \\ s_{21}^{(1)} & s_{22}^{(1)} \end{bmatrix}^{-1} \begin{bmatrix} x_1 - x_1^{(1)} \\ x_2 - x_2^{(1)} \end{bmatrix}$$

$$D_2^2(x_1, x_2) = (x_1 - x_1^{(2)}, x_2 - x_2^{(2)}) \begin{bmatrix} s_{11}^{(2)} & s_{12}^{(2)} \\ s_{21}^{(2)} & s_{22}^{(21)} \end{bmatrix}^{-1} \begin{bmatrix} x_1 - x_1^{(2)} \\ x_2 - x_2^{(2)} \end{bmatrix}$$

Expression 1

The Mahalanobis distances to the disappointment and non-disappointment groups are calculated in this way, and to which of disappointment and non-disappointment the signal waveform is similar is judged (S2004). It is known that the judgment employing Mahalanobis distance exhibits higher identification ability than judgment by merely referring to the degree of correlation.

To which of disappointment and non-disappointment the signal waveform is similar is judged with the use of the thus obtained Mahalanobis distances (S1507). It is known that the judgment employing Mahalanobis distance exhibits higher identification ability than judgment by merely referring to the degree of correlation.

When it is judged that the measured signal waveform is similar to disappointment (Yes in S1507), it is judged that the disappointment signal is detected, namely, the user is disappointed (S1507), and the number n of repetitions of the disappointment trial is incremented (S1519). On the other hand, when it is judged that the measured signal waveform is similar to non-disappointment (No in S1507), it is judged that the disappointment signal is not detected, namely, the user obtains a response as hi/she expected (S1518).

In the case where the number n of repetitions of the disappointment trial is two or larger, the measured signal waveform is compared with the non-disappointment template and a corresponding one of the disappointment templates for the first stage to the fourth stage, and Mahalanobis distances are calculated for identification (S1508 to S1516). Wherein, when the number n is four or smaller, the template for the first stage is used; when the number n is between 5 and 8, both inclusive, the template for the second stage is used; when the number n is between 9 and 12, both inclusive, the template for the third stage is used; and when the number n is 13 or larger, the template for the fourth stage is used.

Figure 19:
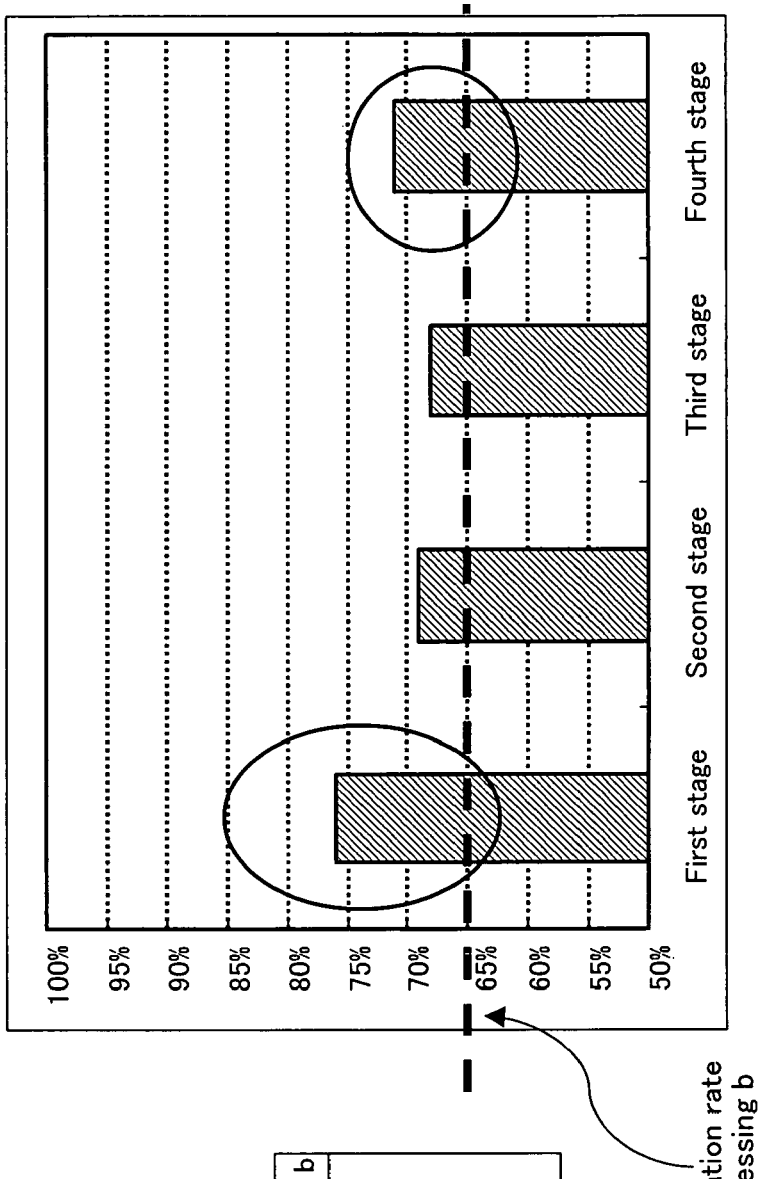
FIG. 19(a) is a table indicating the relationship between difference in processing and the identification rates.
FIG. 19(b) is a graph showing variation in identification rate according to difference in processing.
Figure 20:
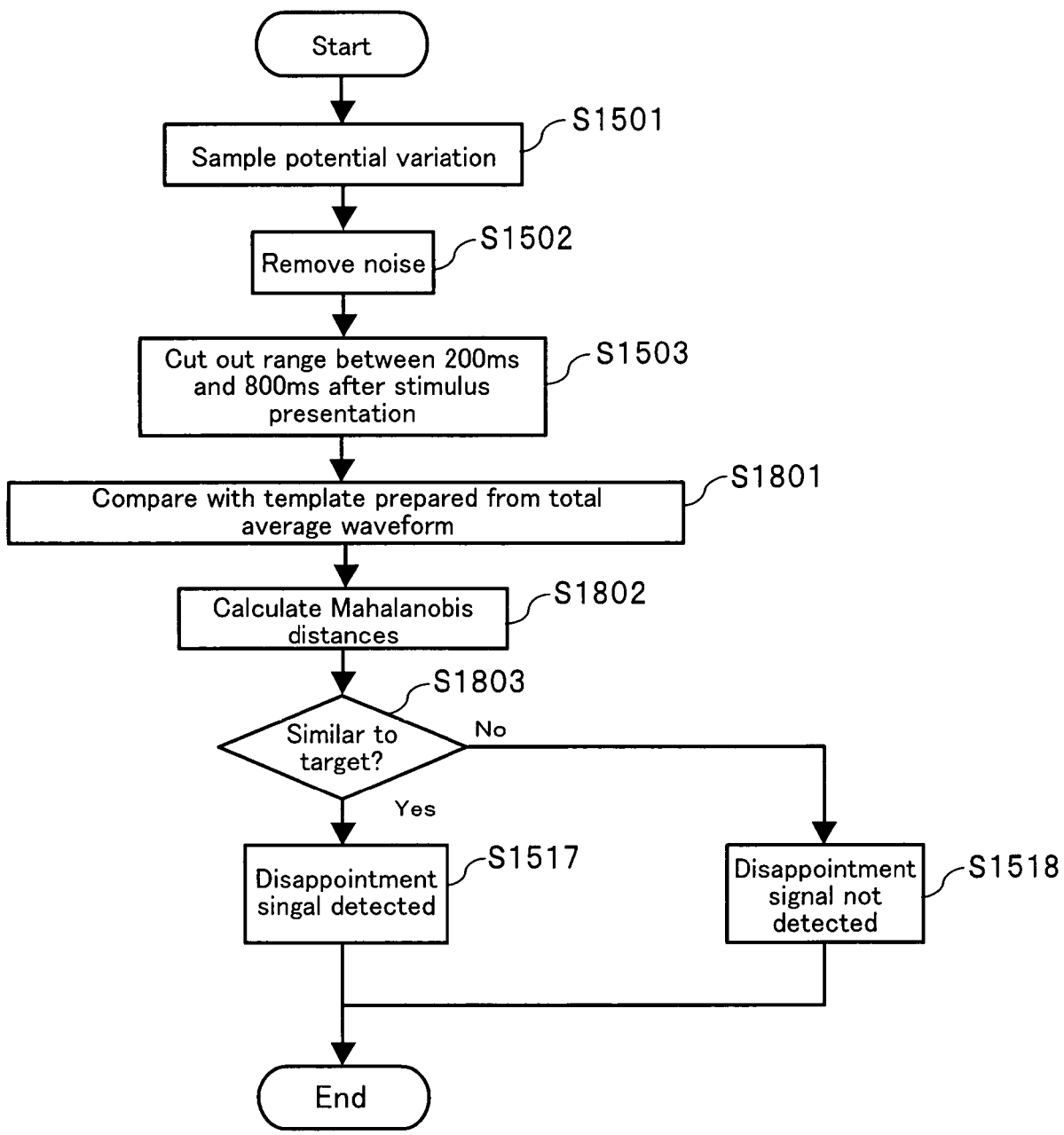
FIG. 20 is a flowchart of judgment using a single template.

FIG. 19 indicates identification rates of disappointment signals obtained by the processing a. For comparison, FIG. 19 also indicates identification rates thereof obtained by a processing b which uses templates for identification prepared by respectively averaging the non-disappointment signals and all the disappointment signals shown in FIG. 15 irrespective of the number of repetitions of disappointment. The method of the processing b is depicted in FIG. 20, wherein the same reference numerals are assigned to the same steps as those in FIG. 18 for omitting the description thereof. Difference from the processing a depicted in FIG. 18 lies in that the judgment standard is not changed and a single template is used even when the number of repetitions of the disappointment trial is increased. The table of FIG. 19(*a*) summarizes identification rates in the case where the judgment standard is changed according to the stage of the disappointment trial and the case where the judgment standard is not changed. The processing a attains 11% and 6% increases in identification rate in the first stage (the initial stage) and the fourth stage (the final stage), respectively, when compared with the identification rate in the processing b. In the processing b, only 15% increase in identification rate can be attained by preparing templates, calculating correlation coefficients, and then calculating Mahalanobis distances in correlation coefficient space. From this, each increase in identification rate in the first stage and the fourth stage, which is attained by the present invention in which the judgment standard is changed according to disappointment state, is significant, and accordingly, this judging method might be useful in the case where disappointment occurs plural times.

The number of repetitions of disappointment is divided into the four stages in the above example, but the present invention is not limited thereto.

It should be noted that for preparing templates according to the number of times (stages) of disappointment, it is essential to select a part of the number of repetitions of disappointment where the amplitude of the disappointment signal decreases steeply or the latency thereof is shortened suddenly. The amplitude of the disappointment signal decreases steeply or the latency thereof is shortened suddenly in a part where disappointment is repeated about 20 times, and therefore, it is preferable to prepare templates for plural stages into which the repetition part up to twentieth disappointment is divided.

In lieu to employment of the templates or together with the templates, another method (a judgment standard) may be employed. For example, in the case where judgment is performed on the basis of a maximum value of the amplitude of the disappointment signal component, the presence or absence of the disappointment signal can be judged on the basis of a value calculated by multiplying a decrease rate of the maximum amplitude in each stage by a maximum value of the amplitude of the first stage.

(Variation in Event-Related Potential by Consecutive Stimuli)

Figure 21:
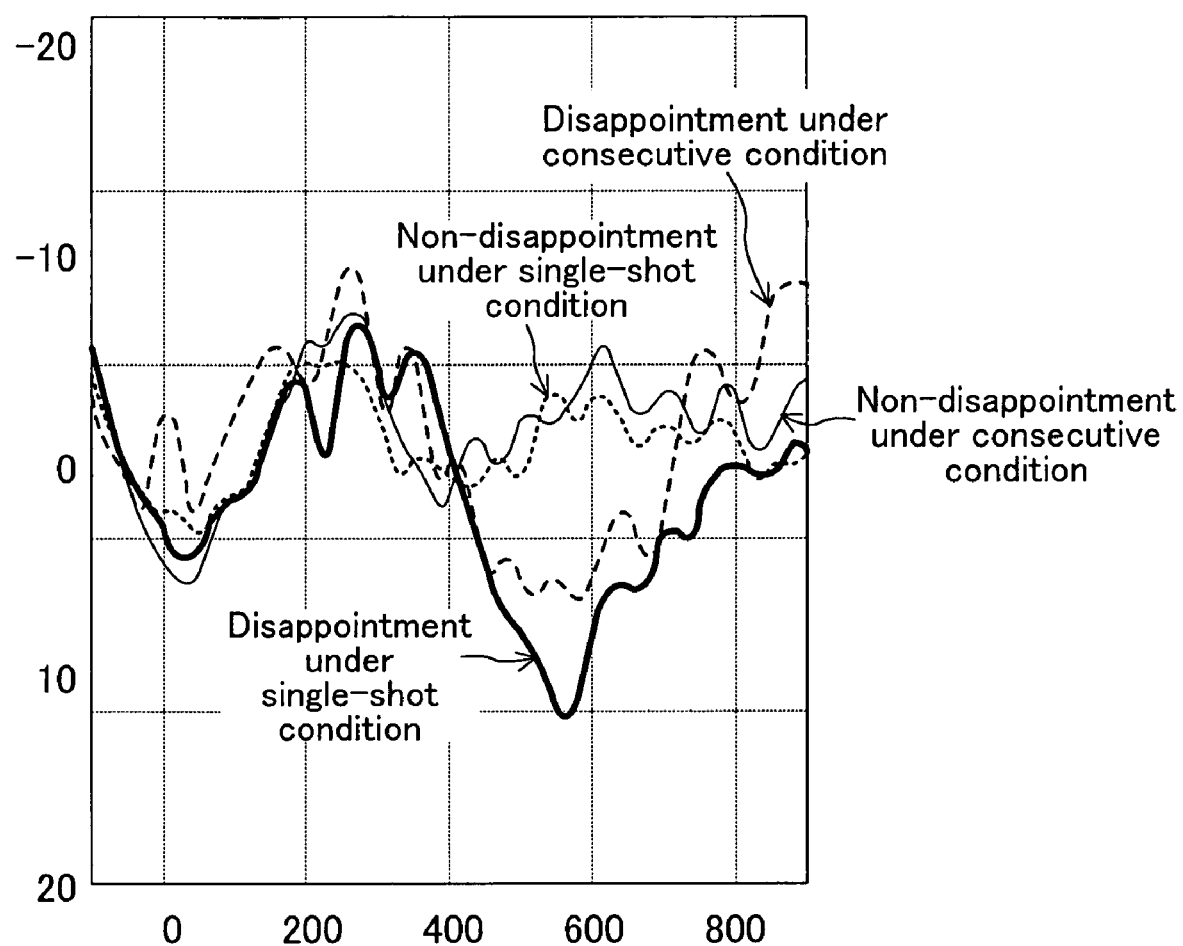
FIG. 21 is a graph showing an average waveform of a disappointment signal under a consecutive condition.
Figure 22:
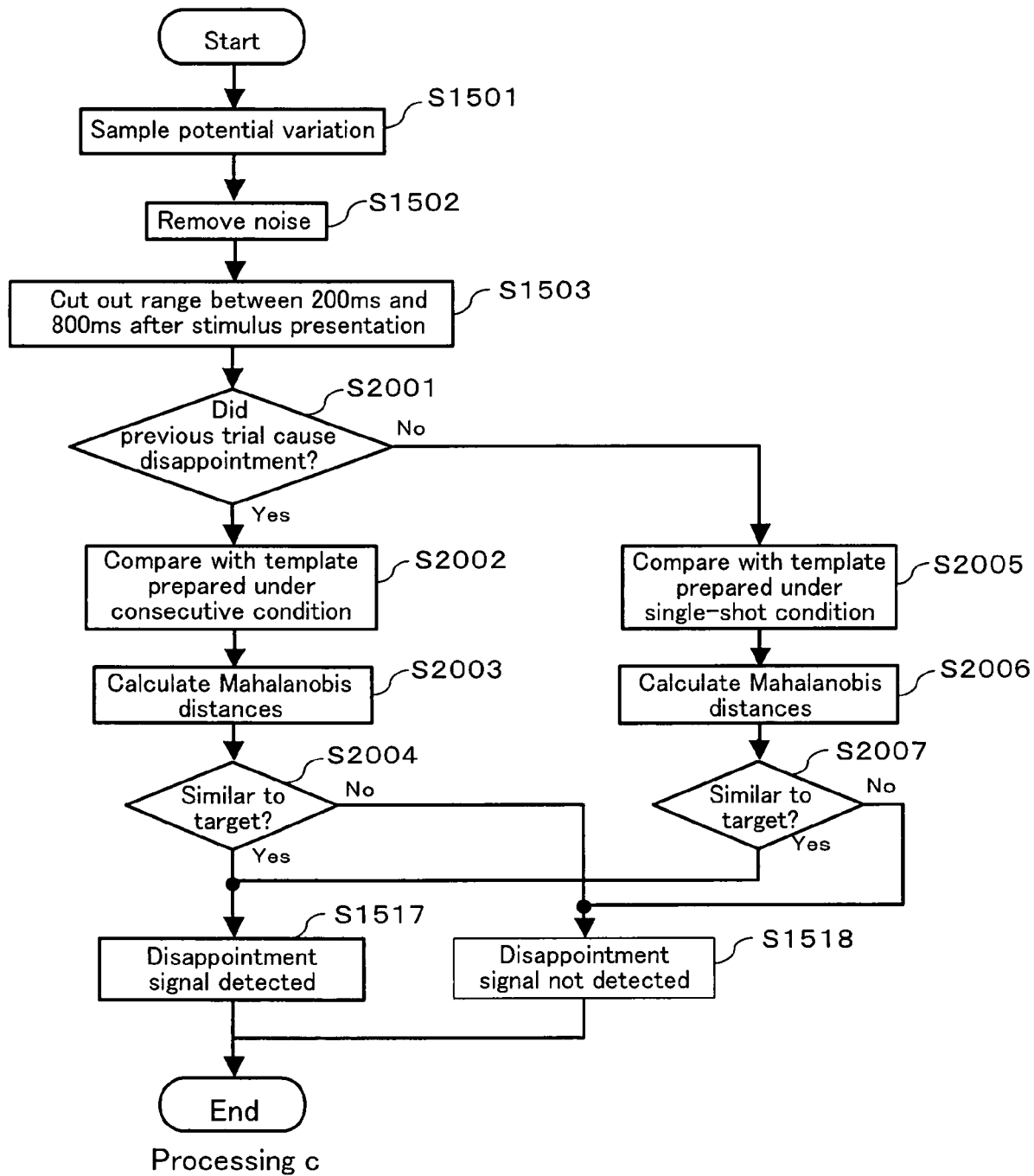
FIG. 22 is a flowchart depicting a procedure for changing the judgment standard under the consecutive condition.

The description has been given hitherto to variation in disappointment signal component when disappointment occurs plural times in a series of appliance manipulation. Besides this, the present inventors newly found that variation in disappointment signal component appears when disappointment occurs consecutively (consecutive condition). In FIG. 21, a bold solid line and a rough broken line indicate an average waveform of disappointment signals obtained by averaging 68 disappointment signals under a single-shot condition and an average waveform thereof obtained by averaging 12 disappointment signals under the consecutive condition, respectively, wherein the single-shot condition means a condition where disappointment occurs discontinuously. As well, an average waveform of the non-disappointment signals obtained by averaging 76 disappointment signals under the consecutive condition and an average waveform thereof obtained by averaging 64 disappointment signals under the single-shot condition are indicated by a thin solid line and a fine broken line, respectively. In FIG. 21, the axis of abscissas indicates time in the unit of ms while the axis of ordinates indicates potential in the unit of $\mu V$. FIG. 21 shows that little difference is observed between the non-disappointment signal under the single-shot condition and that under the consecutive condition while the amplitude of the disappointment signal is reduced under the consecutive condition when compared with that under the single-shot condition. From these results, it can be said that the disappointment signal component varies when disappointment occurs consecutively, and therefore, change of the judgment standard according to whether or not disappointment occurs consecutively, as shown in FIG. 22, might increases the identification FIG. 22 is a flowchart of an example (processing c) of a concrete method for detecting a disappointment signal by changing the judgment according to whether or not disappointment in this time occurs under with the consecutive condition. FIG. 18 shows the processing a in which the judgment standard is changed according to the number of repetitions of disappointment, and therefore, the same reference numerals are assigned to steps of performing the same steps as in FIG. 18 for omitting the description thereof. Difference from FIG. 18 lies in that the judgment standard is changed according to whether or not disappointment in this time occurs under the consecutive condition. The processing c will be described below in order.

First, a template to be used for comparison is selected according to whether or not the previous trial causes disappointment (S2001). If the previous trial causes disappointment, correlation coefficients to, for example, a disappointment template prepared under the consecutive condition and to the non-disappointment template are calculated (S2002). This correlation calculation calculates each degree of correlations between the signal waveform and the respective templates.

Subsequently, the distances from the signal waveform to the disappointment template under the consecutive condition and to the non-disappointment template are calculated (S2003). Mahalanobis distance is employed for this distance calculation, for example. Mahalanobis distance indicates a distance to the center of gravity of a group, data of which variance and covariance are taken into consideration.

In the case under the single-shot condition where the previous trial causes no disappointment, as well, the signal waveform is compared with the disappointment template under the single-shot condition and the non-disappointment template, and respective Mahalanobis distances are calculated for identification (S2005 to S2007).

As described above, when the judgment standard is changed under the consecutive condition so as to correspond to variation in disappointment signal component appearing when disappointment occurs consecutively, the identification rate might increase even under the consecutive condition.

Embodiments of the present invention will be descried below on the basis of the disappointment judging method described hitherto.

As described above, when the disappointment signals of experimental data obtained from the experiment for obtaining the disappointment signals are identified through the processing a (in which the judgment standard is changed according to the repetition stage of the disappointment trial), the identification rates of the disappointment signals in the first stage and the fourth stage increased obviously when compared with those through the processing b. This aspect leads to a conclusion that the present method is useful in the case where disappointment occurs plural times, such as the case where a user who does not know how to use an appliance manipulates the appliance, in the case where many questions of which field a user is not good at are presented in learning through a learning system that feedbacks true/false evaluation upon input of a reply, and the like. The disappointments in the first stage and the fourth stage, of which identification rates have increased by the present method, correspond to an appliance operation that causes disappointment first and an appliance operation that causes disappointment repeatedly, respectively, and both the stages might serve as significant disappointment judgment standards when the disappointment signal is applied to the below described appliances and the like. The same is applied to the disappointment judgment under the consecutive condition.

EMBODIMENT 1

Figure 13:
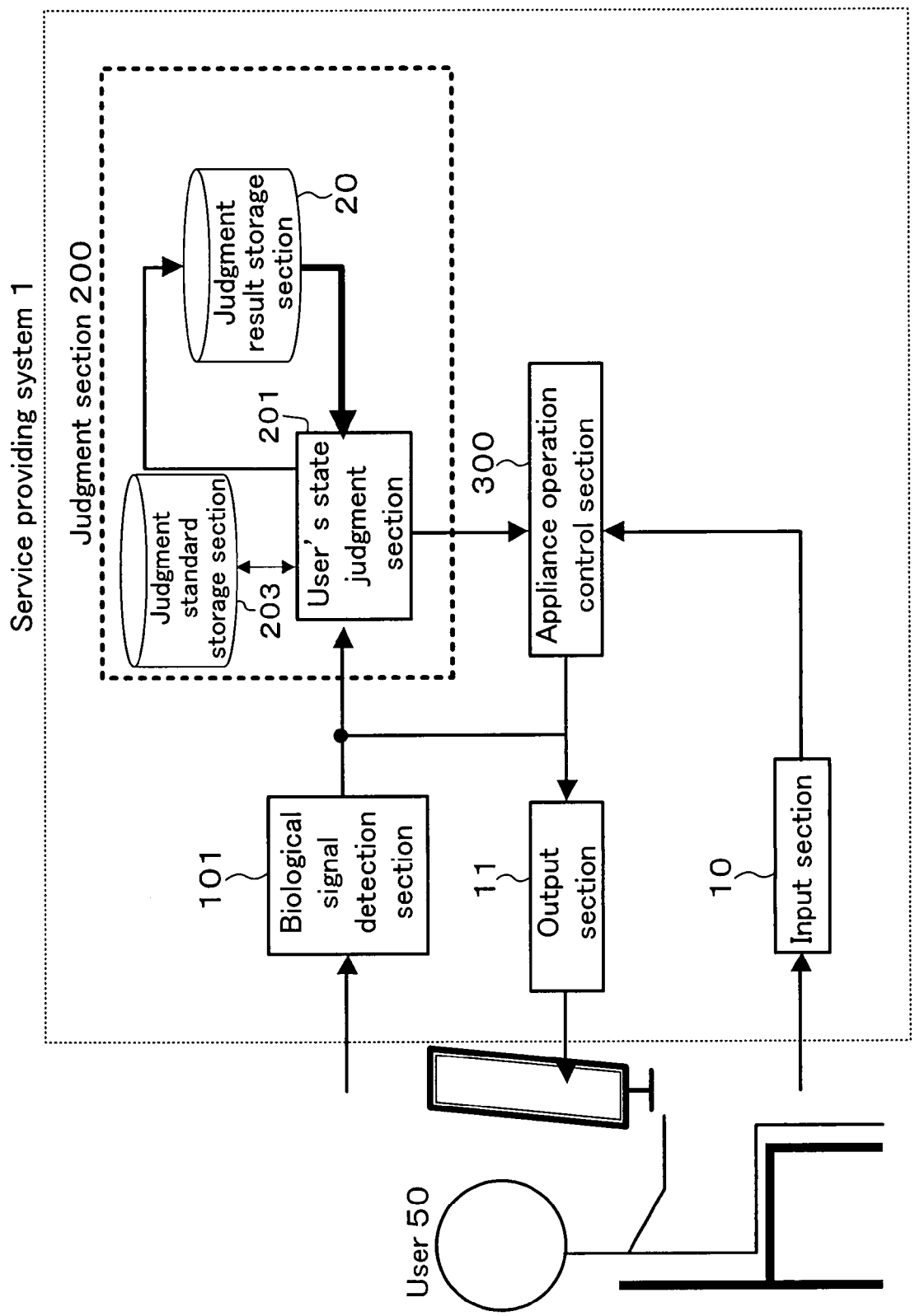
FIG. 13 is an illustration showing a construction of a service providing system according to Embodiment 1.

FIG. 13 is an illustration showing a constitution of a service providing system 1 according to Embodiment 1. In FIG. 13, a biological signal detection section 101 measures an electroencephalogram of a user 50. Upon receipt of user's request from an input section 10, an appliance operation control section 300 determines a response content, and an output section (presentation section) 11 presents the determined response content. In a judgment section 200, a user's state judgment section 201 judges, on the basis of judgment results stored in a judgment result storage section 20, the presence or absence of the specific event-related potential (the disappointment signal) in the event-related potential of the electroencephalogram detected by the biological signal detection section 101 which appears after a predetermined period beginning at a timing as a starting point when the output section 11 presents the response content.

The judgment result storage section 20 stores a history of presence/absence of the disappointment signal judged by the user's state judgment section 201. This history includes the number of occurrences of the specific event-related potential appearing in the past. The user's state judgment section 201 can obtain the number of occurrences of the specific event-related potential appearing in the past by referring to the judgment result storage section 20. Further, a judgment standard storage section 203 stores, for example, waveform data of the event-related potential in the form of a template as a judgment standard for judging the presence or absence of the specific event-related potential. Herein, the judgment standard storage section 203 stores a plurality of templates according to the number of occurrences of the specific event-related potential. The user's stage judgment section 201 selects any of the templates stored in the judgment standard storage section 203 according to the number of occurrences of the specific event-related potential which is obtained by referring to the judgment result storage section 20, and judges the presence or absence of the specific event-related potential with the use of the selected templates.

It is noted that the elements other than the biological signal detection section 101 in the service providing system 1 may be composed of a general personal computer.

With the above arrangement, the presence or absence of the specific event-related potential (the disappointment signal) is judged accurately.

In the present embodiment, a service providing method is provided which includes: a step A of receiving user's request; a step B of determining a response content in response to the request; a step C of presenting the determined response content to the user; a step D of measuring the event-related potential of user's electroencephalogram as user's biological signal; and a step E of judging the presence or absence of the specific event-related potential in the measured event-related potential which would appear after a predetermined period beginning at a timing as a starting point when the response content is presented. Wherein, the step E includes: a sub-step of obtaining the number of occurrences of the specific event-related potential by referring to the history of the judgment results; and a sub-step of determining a judgment standard to be used for judging the presence or absence of the specific event-related potential according to the number of occurrences thereof obtained by the former sub-step and judging the presence or absence of the specific event-related potential with the use of the determined judgment standard. This service providing method can be reduced to practice, except the step D, by allowing a computer to execute a program.

EMBODIMENT 2

Embodiment 2 relates to an appreciation degree judgment system (a kind of service providing system) in which the appliance operation control section 300 of the service providing system 1 shown in FIG. 13 serves as a learning system that feedbacks true/false evaluation automatically upon input of a reply.

User's appreciation degree can be judged in detail in such a manner that the presence or absence of disappointment signal in the event-related potential measured from feedback of true/false evaluation as a starting point is judged, and a correct reply by "guesswork" is detected according to the true/false evaluation of the reply and the presence or absence of the disappointment signal. The appreciation degree judging system using the disappointment signal can judge the user's insufficient appreciation by detecting a correct reply by "guesswork," which has been overlooked conventionally, particularly in multiple-choice questions and the like, so that presentation of review questions is enabled, for example, to increase the learning efficiency. In learning using such a learning system, the user replies to presented questions sequentially and receives feedback of true/false evaluation sequentially. In the case where many questions of which field the user is not good at are presented, disappointment where "a reply which the user had thought wrong was correct" in feedback of true/false evaluation would be caused plural times. For providing countermeasures thereto, the judgment standard is changed according to the number of repetitions of disappointment in order to identify the disappointment signal accurately.

FIG. 1 is an illustration showing a construction of the appreciation degree judgment system 100 according to the present embodiment. In FIG. 1, a biological signal detection section 101 measures an electroencephalogram of a user 50 replying a question. A presentation section 102 selects and presents to the user 50 appropriate one of questions, a true/false judgment result in response to user's 50 reply, and the like. An input section 103 receives user's 50 requests (a reply or the like herein). A user's state judgment section 201 judges whether or not the event-related potential of the electroencephalogram measured by the biological signal detection section 101 from a timing as a starting point when true or false in response to user's 50 reply is presented at the presentation section 102 is the disappointment signal (the specific event-related potential).

A judgment section 200 judges user's state based on the event-related potential of the electroencephalogram measured by the biological signal detection section 101 from a timing as a starting point when true or false in response to user's 50 reply is presented at the presentation section 102.

The user's state judgment section 201 judges whether or not the event-related potential of the electroencephalogram measured by the biological signal detection section 101 from a timing as a starting point when true or false is presented in response to user's 50 reply at the presentation section 102 is the disappointment signal by referring to a history of presence/absence of the disappointment signal (the number of occurrences of disappointment) stored in a judgment result database 202 as a judgment result storage section.

The judgment result database 202 stores the history of presence/absence of the disappointment signal judged by the user's state judgment section 201. FIG. 2 indicates a concrete example of the history stored in the judgment result database 202. As indicated in FIG. 2, the judgment result database 202 stores, for example, manipulation times, manipulation contents, disappointment presence/absence (1 as presence and 0 as absence), and the number n of repetitions (occurrences) of disappointment. The number n of repetitions of disappointment may be initialized according to the usage state of the appreciation degree judgment system 100. It may be initialized, for example, when input to the appreciation degree judgment system 100 is interrupted for one hour, when the power source of the appreciation degree judgment system 100 is turned OFF, when the field of questions for learning is change, or the like. The history of presence/absence of the disappointment signal stored in the judgment result database 202 is used in the next user's state judgment where the user 50 replies to questions successively.

For judging the user's state by referring to the history of presence/absence of the disappointment signal, for example, a plurality of templates (waveform charts of the event-related potential) prepared according to the number of repetitions of disappointment or the like are stored as judgment standards in the judgment section 200, and with which template the present event-related signal should be compared is determined on the basis of the number n of repetitions of disappointment stored in the judgment result database 202. To do so, the judgment section 200 includes a judgment standard storage section 203 for storing the templates as the judgment standards.

FIG. 3 shows concrete examples of numerical values of the templates (aggregation of position coordinates of points represented as a waveform chart) stored in the judgment standard storage section 203. For the four disappointment templates indicated in FIG. 3, the aforementioned experiment for obtaining disappointment signals is performed in advance, and the potential samples in the range, for example, between 200 ms and 800 ms after stimulus presentation are divided according to the number of repetitions of disappointment in the procedure as depicted in FIG. 16 and are averaged. The rule (the processing a depicted in FIG. 18, for example) for changing the template according to the number of repetitions of disappointment is set and stored in advance in the user's state judgment section 201.

The user's state judgment section 201 obtains the number n of repetitions of disappointment by referring to the judgment result database 202. Then, it selects templates in accordance with the template changing rule and calculates the correlation coefficients between the thus selected templates and the potential variation in this time. Specifically, for example, when the number n of repetition time of disappointment is one, the disappointment template 1 and the non-disappointment template are selected, and the correlation coefficients between the respective templates and the potential variation in this time are calculated with the use of Expression 2. In Expression 2, r is a correlation coefficient, n is a number of samples of templates, x is a detected event-related potential, $x_i$ is an i-th potential sample within the range where the correlation coefficient is to be calculated, y is template data, $y_i$ is i-th template data, and ave(x) and ave(y) are average values of x and y, respectively.

[Expression 2]

$$r = \frac{\frac{1}{n}\sum_{i=1}^{n}(x_i - ave(x))(y_i - ave(y))}{\sqrt{\frac{1}{n}\sum_{i=1}^{n}(x_i - ave(x))^2}\sqrt{\frac{1}{n}\sum_{i=1}^{n}(y_i - ave(y))^2}}$$ [Expression 2]

As well, when the number n of repetitions of disappointment is five, for example, the disappointment template 2 and the non-disappointment templates are selected by changing the disappointment template 1 to the disappointment template 2, and the correlation coefficients between the respective templates and the potential variation in this time are calculated. It is noted that Mahalanobis distances computed from the calculation result of the correlation coefficients as in Expression 1 may be employed for identification. In both the cases, two templates of the non-disappointment template and any one of the disappointment templates (any one of templates 1 to 4) are selected to be used as the judgment standards.

As described above, the judgment by changing the template according to the number n of repetitions of disappointment is the difference of the present embodiment from Patent Document 1. Template change according to transition of user's state increases the identification rate of the disappointment signal.

Alternatively, the judgment standard storage section 203 may store, as another disappointment template, a consecutive disappointment template which is a template of the total average of detected disappointment signals. When the disappointment history stored in the judgment result database 202 indicates that the previous trial has caused disappointment, namely, when it is judged that the specific event-related potential was present in the previous judgment, the user's state judgment section 201 may calculate the correlation coefficients with the disappointment template changed to the consecutive disappointment template. The consecutive disappointment template corresponds to a for-consecutiveness judgment standard for judging disappointment which is to be used in the case where the specific event-related potential is detected consecutively. Trial in which judgment is performed with the consecutive disappointment template selected are indicated as the mark*in FIG. 2. Patent Document 1 is silent about this judging method.

Figure 6:
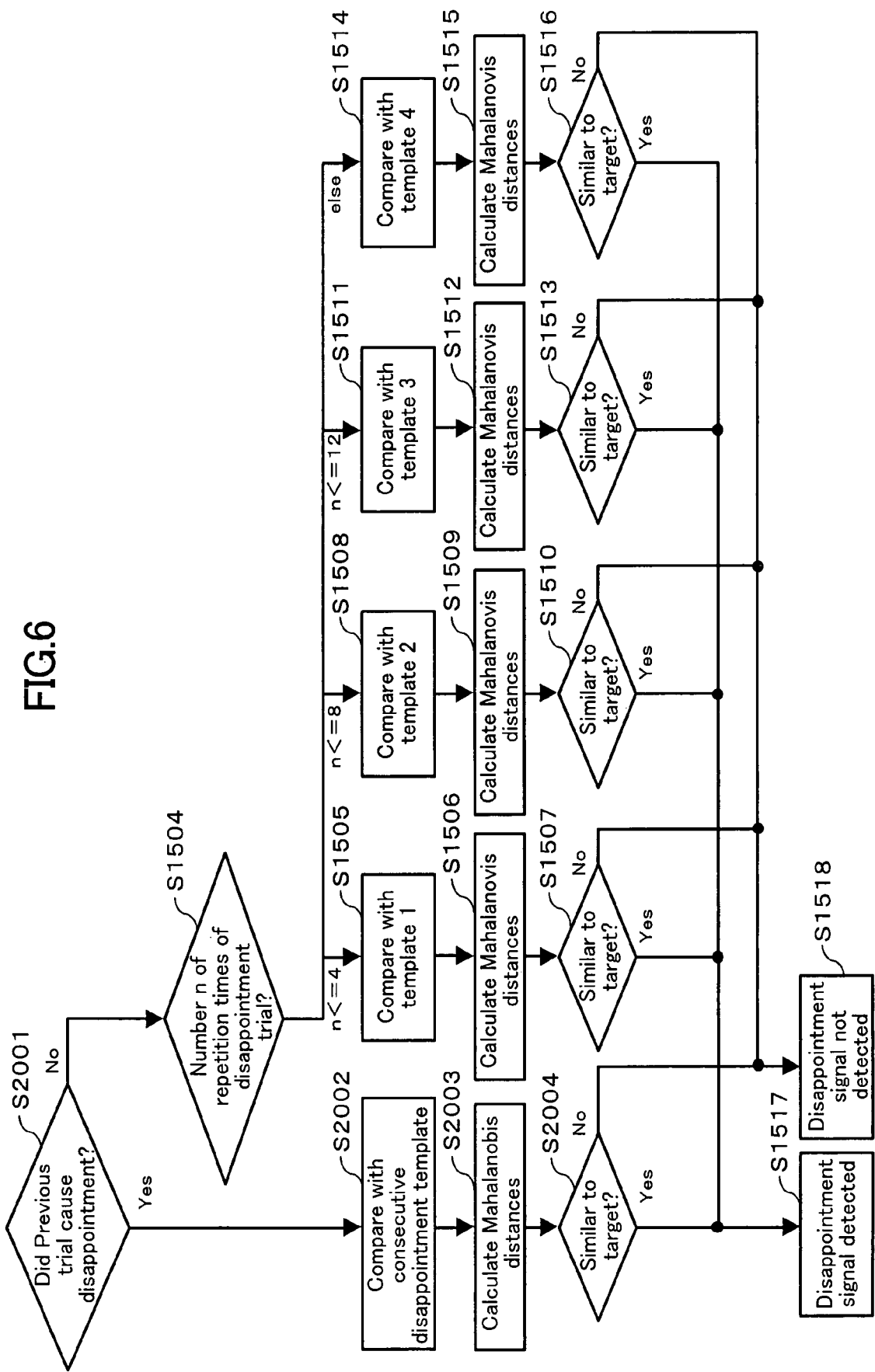
FIG. 6 is a flowchart depicting an example of a user's state judging method.

Optionally, the judgment standard storage section 203 may store, as shown in FIG. 5, a consecutive disappointment template indicated in FIG. 4 as a disappointment template, in addition to the templates 1 to 4 indicated in FIG. 3. In this case, the user's state judgment section 201 performs judgment by the procedure depicted in the flowchart of FIG. 6. In FIG. 6, when disappointment has not been detected in the previous trial (No in S2001) in the flow for consecutive disappointment detection depicted in FIG. 22, the steps using a single template depicted as S2005 to S2007 are replaced by the steps depicted as S1504 to S1516 in FIG. 18 in which the template is changed according to the number of times of disappointment. Each step is the same as that depicted in FIG. 18 and FIG. 22, and therefore, the same reference numerals are assigned for omitting the description thereof.

Alternatively, it is possible that any of the four stages is selected according to the number of occurrences of disappointment up to this time in the flowchart depicted in FIG. 18 rather than the flowchart depicted in FIG. 6, and then, whether or not the disappointment signal has been detected in the previous trial is judged in the selected stage. In the case where the disappointment signal has been detected in the previous trial, the consecutive disappointment template is selected as a judgment standard, and Mahalanobis distances are calculated. Otherwise, namely, when the previous trial has not cause disappointment, the judgment is performed in such a manner that a corresponding template is selected and Mahalanobis distances are calculated. In this case, only one consecutive disappointment template may be provided, or the consecutive disappointment template may be provided in each stage.

An appliance operation control section 300 receives user's 50 reply from the input section 103, performs true/false judgment, and performs appreciation degree judgment on the basis of the presence or absence of the disappointment signal received from the user's state judgment section 201 and the result of true/false judgment. A true/false judgment section 301 judges whether or not the user's 50 reply to the question presented at the presentation section 102, which is received from the input section 103, is correct. A guesswork/delusion judgment section 302 receives outputs from the true/false judgment section 301 and from the user's state judgment section 201 to judge user's 50 appreciation degree regarding the presented question on the basis of true or false of user's replay and the presence or absence of the disappointment signal. A question database 303 stores data relating to questions, such as questions, correct answers, importance of each question, and the like and provides correct answer data of a question to the true/false judgment section 301. FIG. 7 shows a concrete example of the question database 303. A result accumulation database 304 stores user's appreciation degree regarding each question which is judged by the guesswork/delusion judgment section 302. FIG. 8 shows concrete examples of the contents stored in the result accumulation database 304. A question selection section 305 selects and determines a question to be presented next by referring to the question database 303 and the result accumulation database 304. The question database 303 and the question selection section 305 compose a question determination section.

In the appreciation degree judgment system 100 in FIG. 1, the constitutional elements other than the biological signal detection section 101 can be composed by a general personal computer. The constitutional elements other than biological signal detection section 101, the presentation section 102, and the input section 103 can be configured on a network.

The biological signal detection section 101 includes an electroencephalograph which measures an event-related potential of an electroencephalogram as a biological signal. The user 50 fits the electroencephalograph in advance. Optimum points where the electrodes are set may be determined according to an experiment or the like. The measured user's 50 electroencephalogram is sampled so as to be processed by a computer and is sent to the judgment section 200.

The presentation section 102 is composed of a display, a speaker, or the like, and the input section 103 is composed of a keyboard, a mouse, a sound input device, or the like.

The judgment section 200 detects the presence or absence of the disappointment signal in the user's 50 electroencephalogram, which would appear in a predetermined time range after presentation of true/false in response to user's 50 reply, with the use of templates selected by the user's state judgment section 201 from the plurality of stored templates as the judgment standards. The user's state judgment section 201 judges whether or not the event-related potential of the electroencephalogram detected by the biological signal detection section 101 from a timing as a starting point when the representation section 102 presents true or false in response to the user's reply is the disappointment signal (the specific event-related potential) by referring to the history of presence/absence of the disappointment signal (the number of occurrences of disappointment) stored in the judgment result database 202. It is noted that the plurality of stored judgment standards may be prepared through, for example, the procedure depicted in FIG. 16 after the aforementioned experiment for obtaining disappointment signals. Though the disappointment signal component varies by several-time repetition of disappointment, as described above, the above judging method increases the identification rate.

It is noted that the disappointment signal may be detected by the same method as in the aforementioned experiment by calculating Mahalanobis distances, calculating the correlation coefficients, or the like. For detecting the disappointment signal, a part of the biological signal around approximately 600 ms from true/false presentation may be set as a predetermined time range of the templates. The time range around 600 ms may be between 200 ms and 800 ms, between 500 ms and 700 ms, between 300 ms and 900 ms, or the like, or may be between 450 ms and 800 ms, both inclusive, in which the significant difference is recognized in the t-test. Alternatively, it may be a range approximately 1 s from the presentation with no lower limit set.

The guesswork/delusion judgment section 302 judges user's appreciation degree regarding a presented question on the basis of the true/false result in response to user's reply received from the true/false judgment section 301 and the presence or absence of the disappointment signal received from the user's state judgment section 201. FIG. 9 is a table indicating a judgment logic that the guesswork/delusion judgment section 302 employs. In accordance with the table in FIG. 9, whether or not the user 50 appreciates a presented question is judged.

Specifically, as indicated in FIG. 9, in the case where the user's reply is correct, the guesswork/delusion judgment section 302 judges that the user 50 has replied by "guesswork" when the disappointment signal is detected or judges that the user 50 has appreciated the question when the disappointment signal is not detected. On the other hand, in the case where the user's reply is wrong, it judges that that the user's 50 reply has resulted from a "delusion" when the disappointment signal is detected or judges that the user have not appreciated the question when the disappointment signal is not detected. In this way, whether or not a correct reply has been by "guesswork" can be recognized, and whether or not a wrong reply has resulted from a "delusion" can be recognized.

Figure 10:
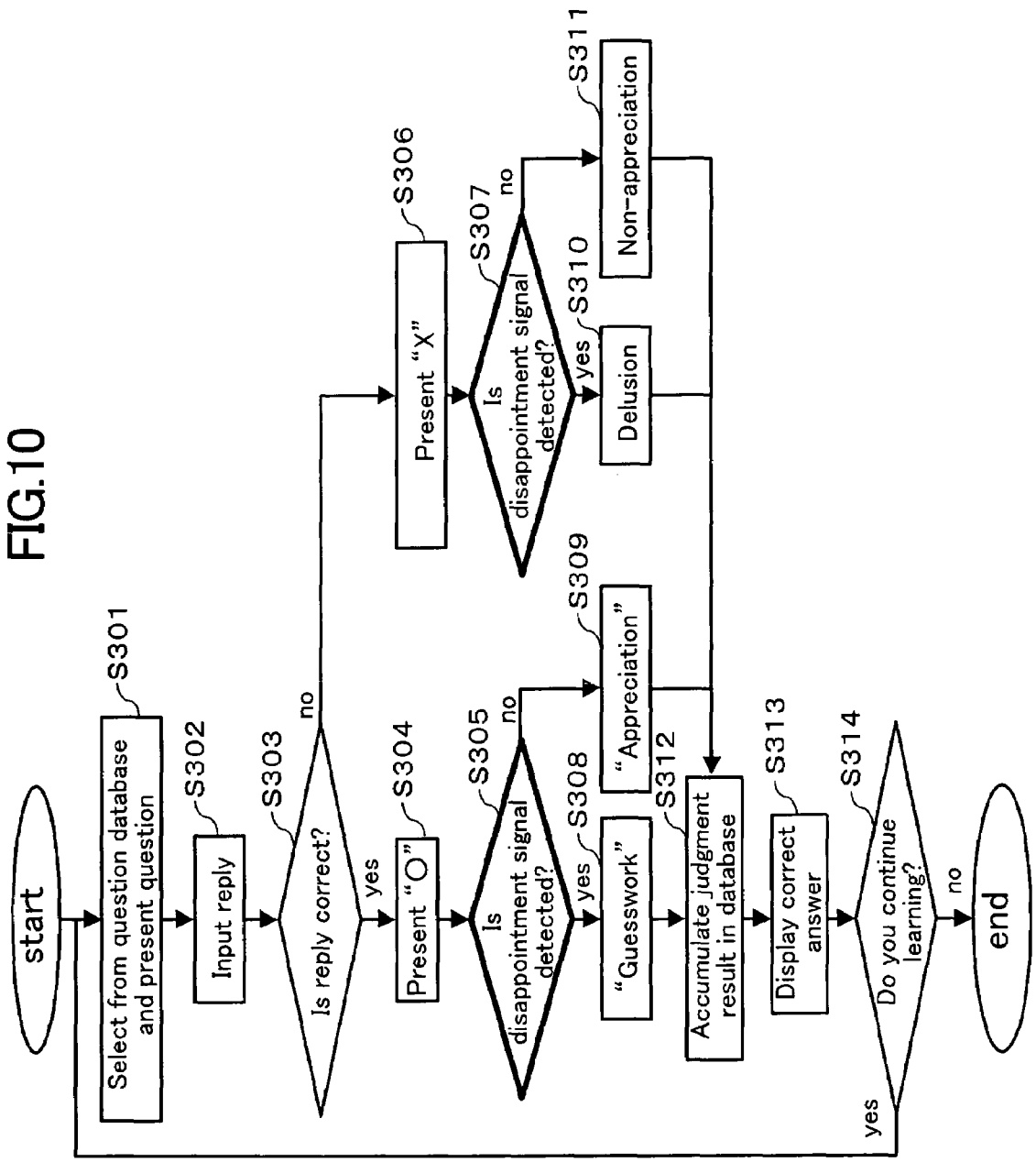
FIG. 10 is a flowchart depicting an operation of the appreciation degree judgment system in FIG. 1.

An operation of the thus configured appreciation degree judgment system according to the present embodiment will be described below with reference to the flowchart of FIG. 10.

First, in a step S301, the question selection section 305 selects a question to be presented next from the questions stored in the question database 303, and the presentation section 102 presents the selected question. Herein, questions may be selected, as shown in FIG. 8, for example, principally from an important field, which the user would less appreciate, according to information on the importance of each question stored in the question database 303 (see FIG. 7), the user's appreciation degree stored in the result accumulation database 304, or the like. This leads to presentation of review questions in the important field which the user 50 would less appreciate.

Subsequently, the user 50 replies to the question presented in the step S301. This reply is input to the appreciation degree judgment system 100 through the input section 103 (S302). The true/false judgment section 301 compares the reply received from the input section 103 with the question's correct answer stored in the question database 303 for judging true or false of the user's reply (S303). When the reply is correct (yes in S303), the routine proceeds to a step S304. When the reply is wrong (no in S303), the routine proceeds to a step S306.

When the reply is correct, that the reply is correct is presented to the user 50 through the presentation section 102. For example, in the case where the presentation section 102 is a display, "○" or the like is displayed. The timing of this presentation serves as a trigger for disappointment signal detection. Then, the user's state judgment section 201 detects the presence or absence of the disappointment signal in the biological signal measured by the biological signal detection section 101 (S305). For detection, the judgment standard is changed according to the number of repetitions of user's disappointment and/or according to whether or not disappointment occurs consecutively.

In a step S308, the guesswork/delusion judgment section 302 judges that the correct reply has been by "guesswork." The disappointment signal is detected even though that the reply is correct is presented, and therefore, the user 50 might have expected presentation of false. Accordingly, it is judged that guesswork by the user 50 who does not appreciate the presented question resulted in a correct reply by chance. On the other hand, in a step S309, it is judged that the user 50 appreciated the presented question. The disappointment signal is not detected in response to presentation that the reply is correct, and therefore, the user 50 might have expected presentation of true. Namely, the user 50 had thought that the reply is correct rightly.

In contrast, when the reply is wrong, the presentation section 102 presents to the user 50 that the reply is wrong in the step S306. For example, in the case where the presentation section 102 is a display, "X" or the like is displayed. The timing of this presentation also serves as a trigger for disappointment signal detection. Then, the user's state judgment section 201 detects the presence or absence of the disappointment signal in the biological signal measured by the biological signal detection section 101 (S307). For detection, the judgment standard is changed according to the number of repetition of disappointment by following the procedure in FIG. 6. The respective steps in FIG. 6 are the same as the steps depicted in FIG. 18 and FIG. 22, and therefore, the same reference numerals are assigned thereto for omitting the description thereof. When the disappointment signal is detected (yes in S307), the routine proceeds to a step S310. When the disappointment signal is not detected (no in S307), the routine proceeds to a step S311.

In the step S310, the guesswork/delusion judgment section 206 judges that the wrong reply has resulted from a "delusion." The disappointment signal appears when that the reply is wrong is represented, and therefore, the user 50 might have expected presentation of true. Namely, it is judged that the reply that the user 50 had provided with confidence has resulted from "delusion." On the other hand, in the step S311, it is judged that the user 50 had not appreciated the presented question. Because the disappointment signal does not appear when that the reply is wrong is presented, the user 50 might have expected presentation of false. In other words, the user 50 might have though that the reply is wrong.

Next, the judgment results in the steps S308 to S311 are accumulated in the result accumulation database 304 (S312). For accumulating the judgment results, a label indicating a judgment result, that is, "guesswork," "appreciation," "delusion," or "non-appreciation" is stored for each question, for example. Alternatively, weight coefficients according to the appreciation degrees as shown in FIG. 11 may be stored. In the example shown in FIG. 11, the weight coefficients are set so that when the user's appreciation is insufficient (when user's reply is resulted by "guesswork," results from "delusion," or results from "non-appreciation"), a possibility that the same question is selected again is increased for reviewing.

In a step S131, the true/false judgment section 301 reads out the correct answer regarding the previously presented question from the question database 303, and the presentation section 102 displays the read-out answer.

Thereafter, the user 50 selects whether or not the user continues learning (S314). When continuation of learning is input to the input section 103, the routine returns to the step S301 to present the next question.

With the use of the above described appreciation degree judgment system that performs judgment based on the presence or absence of the disappointment signal and true/false regarding replies, four kinds of states of "guesswork," "appreciation," "delusion," and "non-appreciation" can be recognized from a reply, which can have been classified into only two of "correct reply" and "wrong reply" conventionally. This enables a correct reply by "guesswork," which has been judged as "appreciation" and has been overlooked conventionally, to be judged as insufficient appreciation, and accordingly, appropriate countermeasures thereto, such as presentation of review questions can be provided. Thus, the leaning efficiency might increase.

In contrast, in the case where the disappointment judgment standard is not changed regardless of transition of user's state as above, the disappointment detection rate is low in disappointment in the first stage (the initial stage), the fourth stage, and disappointment under consecutive condition, resulting in an increase in possibilities of misjudgment of "guesswork" as "appreciation" and misjudgment of "delusion" as "non-appreciation." Detection of the disappointment especially in the first stage (the initial stage) is significant in the appreciation degree judging system in which an increase in learning efficiency is contemplated in such a manner that the frequency of presenting review questions in the field that the user has been already "appreciated" is lowered by classifying the user's appreciation degree into "guesswork," "appreciation," "delusion," and "non-appreciation" with the use of the event-related potential.

An increase in identification accuracy of the disappointment signal in the first stage (the initial stage) by changing the judgment standard according to transition of user's state as in the aforementioned processing a leads to an increase in learning efficiency in learning using the appreciation degree judgment system.

EMBODIMENT 3

Embodiment 3 of the present invention relates to a service providing system disclosed in Patent Document 1 which provides services in conformity with user's request by changing a service provision content upon detection of the disappointment signal, such as a home use robot, an information terminal, a home appliance or the like. It takes a considerable training period for the user to be able to address such a user adaptive service providing system. The service providing system provides services to the user again and again in such a training period, and therefore, the disappointment signal might appear plural times in the training period. For providing better adaptation to the user, it is necessary to identify accurately the disappointment signal especially in the fourth stage (the final stage), and hence, the aforementioned judging method is employed in which the judgment standard is changed according to the number of repetitions of disappointment.

Figure 12:
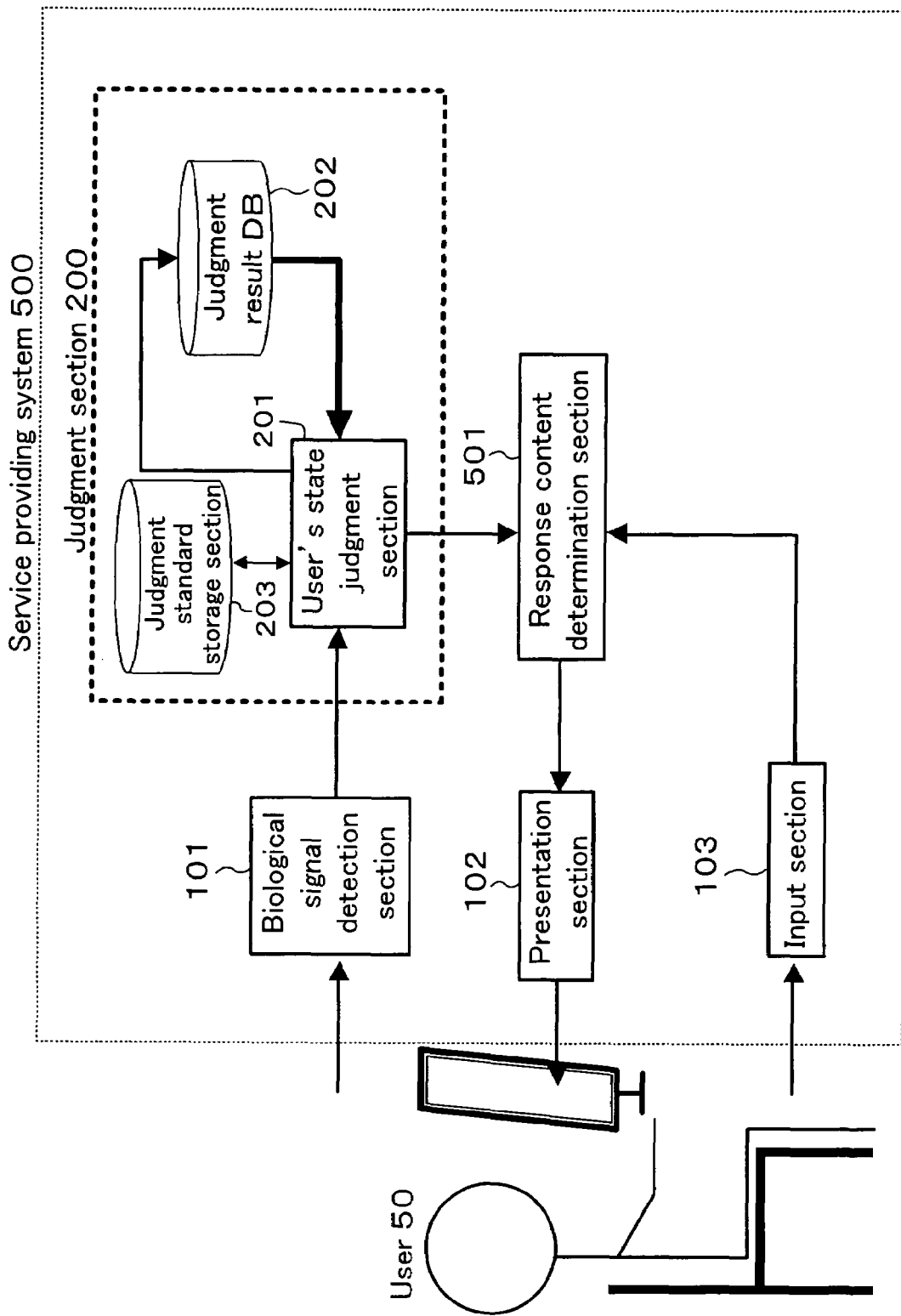
FIG. 12 is an illustration showing a construction of a service providing system according to Embodiment 3.

FIG. 12 is an illustration showing a construction of a service providing system 500 according to the present embodiment. The same reference numerals are assigned to the constitutional elements common to those in FIG. 1 for omitting the description thereof. Difference from FIG. 1 lies in that the appliance operation control section 300 is renamed a response content determination section 501 for determining a response content according to the presence or absence of the disappointment signal.

In the service providing system 500, which changes services when system's services provided in response to user's request is not one the user expected, it is significant to detect the disappointment signal especially in the fourth stage (the final stage) for better adaptation. The fourth stage (the final stage) corresponds to a stage where the user has learned that disappointment where the services provided by the system is not in conformity with the user's request would be repeated. Unless disappointment in the fourth stage (the final stage) is detected, the appliance's services are not changed any more, disabling service provision in conformity with the user's request. Further, user adaptation does not progress any more.

In the case, as in the processing a, where user's state transfers in the course of service provision that causes disappointment plural times, the judgment standard is changed according to transition of the user's state to increase the identification accuracy of detection of the disappointment signal in the fourth stage (the final stage), enabling provision of services in further conformity with user's request.

OTHER EMBODIMENTS

The above described embodiments are mere examples of the present invention, and the present invention is not limited thereto. For example, it is known from experience that immediately after an information terminal, such as a mobile phone, a home appliance, such as a DVD recorder, or the like is changed newly in model, disappointment is caused plural times in the course of many-time trial of manipulation of the information terminal or the home appliance. The user has been accustomed to the arrangement of the buttons and the like of the previous mobile phone or the arrangement of the buttons and the like of the remote control for the previous DVD recorder and is not friendly to the arrangement of the buttons and the like of the new model immediately after the model change. Therefore, the user would frequently push a wrong button which is the correct button in the previous model. When the present invention is applied to the judgment of the presence or absence of the specific event-related potential in such the case where the disappointment signal (the specific event-related potential) appears plural times, the presence or absence of the specific event-related potential can be judged reliably. The present invention for judging disappointment by referring to the history of presence/absence of the disappointment signal is applicable to disappointment judgment where disappointment occurs plural times in using an appliance.

Further, in a personal computer or a home appliance, such as a DVD or the like in which "HELP" is displayed automatically, timely indication of "HELP" when HELP is necessary in fact is in conformity with user's expectation. While, when "HELP" is displayed at an unnecessary timing, the user would feel disappointment. The disappointment judging method in the above embodiments can be applied to such a case where HELP is displayed automatically.

INDUSTRIAL APPLICABILITY

The service providing system according to the present invention can detect the disappointment signal accurately even in situations where disappointment occurs repeatedly and where disappointment occurs consecutively, and accordingly, is useful, for example, in a learning support system which might cause disappointment repeatedly, a service providing system in which "HELP" or recommended information is displayed automatically, and the like.

The invention claimed is:

1. A service providing system, comprising:
an input section which receives a request of a user;
an appliance operation control section which determines a response content in response to the request received at the input section;
a presentation section which presents to the user the response content determined by the appliance operation control section;
a biological signal detection section which measures an event-related potential of an electroencephalogram as a biological signal of the user; and
a judgment section which judges presence or absence of a specific related-event potential after a predetermined period beginning at a starting point in the event-related potential measured by the biological signal detection section, the starting point being time when the presentation section presents the response content,
wherein the judgment section includes:
a judgment result storage section which stores a history of a judgment result;
a judgment standard storage section which stores a plurality of judgment standards for judging presence or absence of the specific event-related potential according to number of occurrences of the specific event-related potential; and
a user's state judgment section which obtains number of occurrences of the specific event-related potential by referring to the judgment result storage section, which selects one of the judgment standards in the judgment standard storage section according to the obtained number of occurrences, and which judges presence or absence of the specific event-related potential with use of the selected judgment standard,
wherein the judgment standard storage section further stores at least one for-consecutiveness judgment standard for a case where the specific event-related potential occurs consecutively, and
the user's state judgment section refers to the judgment result storage section, and when it has been judged that the specific event-related potential is present in the previous judgment, the user's state judgment section selects one of the for-consecutiveness judgment standard in the judgment standard storage section and judges presence or absence of the specific event-related potential with use of the selected for-consecutiveness judgment standard.

2. The service providing system of claim 1,
wherein the predetermined period is between 450 ms and 800 ms, both inclusive.

3. The service providing system of claim 2,
wherein the predetermined period is around 600 ms or around 750 ms.

4. The service providing system of claim 1,
wherein the judgment standards are templates prepared on the basis of a result of event-related potential measured in advance.

5. The service providing system of claim 1,
wherein the appliance operation control section determines again or cancel the response content according to presence or absence of the specific event-related potential.

6. A service providing method, comprising:
a step A of receiving a request of a user;
a step B of determining a response content in response to the request;
a step C of presenting the determined response content to the user;
a step D of event-related potential of an electroencephalogram as a biological signal of the user;
a step E of judging presence or absence of a specific event-related potential after a predetermined period beginning at a starting point in the measured event-related potential, the starting point being time when the response content is presented,
wherein the step E includes:
   a sub-step E1 of obtaining number of occurrences of the specific event-related potential by referring to a history of a judgment result; and
   a sub-step E2 of determining, according to the obtained number of occurrences, a judgment standard for judging presence or absence of the specific event-related potential and judging presence or absence of the specific event-related potential with use of the determined judgment standards,
wherein in the sub-step E2, when it has been judged that the specific event-related potential is present in the previous judgment, presence or absence of the specific event-related potential is judged with use of for-consecutiveness judgment standard for a case where the specific event-related potential occurs consecutively.

7. A computer program embedded in a computer readable medium which allows a computer to execute:
   a step A of receiving a request of a user;
   a step B of determining a response content in response to the request;
   a step C of presenting the determined response content to the user; and
   a step B of judging presence or absence of a specific event-related potential after a predetermined period beginning at a starting point in an event-related potential of a measured electroencephalogram of the user, the starting point being time when the response content is presented,
wherein the step E includes:
   a sub-step E1 of obtaining number of occurrences of the specific event-related potential by referring to a history of a judgment result; and
   a sub-step E2 of determining, according to the obtained number of occurrences, a judgment standard for judging presence or absence of the specific event-related potential and judging presence or absence of the specific event-related potential with use of the determined judgment standard,
wherein in the sub-step E2, when it has been judged that the specific event-related potential is present in the previous judgment, presence or absence of the specific event-related potential is judged with use of for-consecutiveness judgment standard for a case where the specific event-related potential occurs consecutively.

* * * * *

UNITED STATES PATENT AND TRADEMARK OFFICE
CERTIFICATE OF CORRECTION

PATENT NO.         : 7,472,036 B2
APPLICATION NO.    : 11/666241
DATED              : December 30, 2008
INVENTOR(S)        : Shinobu Adachi et al.

It is certified that error appears in the above-identified patent and that said Letters Patent is hereby corrected as shown below:

In Column 24, Line 3, (CLAIM 7), change "a step B of" to --a step E of--.

Signed and Sealed this

Nineteenth Day of May, 2009

JOHN DOLL
*Acting Director of the United States Patent and Trademark Office*